US006376169B1

(12) United States Patent
Adams et al.

(10) Patent No.: US 6,376,169 B1
(45) Date of Patent: Apr. 23, 2002

(54) METHOD FOR DIAGNOSING A VASCULAR CONDITION

(75) Inventors: Michael A. Adams, Kingston; Jeremy P. W. Heaton, Gananoque; Charles H. Graham; Susan E. Brien, both of Kingston, all of (CA)

(73) Assignee: Queens University at Kingston, Kingston (CA)

( * ) Notice: Subject to any disclaimer, the term of this patent is extended or adjusted under 35 U.S.C. 154(b) by 0 days.

(21) Appl. No.: 09/302,554

(22) Filed: Apr. 30, 1999

Related U.S. Application Data
(60) Provisional application No. 60/083,763, filed on May 1, 1998.

(51) Int. Cl.[7] .............................. C12Q 1/00; C12Q 1/68; G01N 33/53; G01N 33/48
(52) U.S. Cl. .................. 435/4; 435/7.1; 435/6; 436/64
(58) Field of Search ............... 436/64; 435/4, 435/7.1, 6

(56) References Cited

U.S. PATENT DOCUMENTS

| | | | |
|---|---|---|---|
| 4,968,603 A | * 11/1990 | Slamon et al. | |
| 5,039,608 A | 8/1991 | Goldstein et al. | 435/7.92 |
| 5,688,649 A | 11/1997 | Croce et al. | 435/6 |
| 5,688,658 A | 11/1997 | Diamandis | 435/7.23 |
| 5,700,447 A | 12/1997 | Bucala et al. | 424/9.1 |
| 5,733,790 A | 3/1998 | Potter et al. | 436/518 |
| 5,804,392 A | 9/1998 | Esmon et al. | 435/7.1 |
| 5,814,462 A | 9/1998 | Weinberger | 435/7.1 |
| 5,912,135 A | 6/1999 | Luderer et al. | 435/7.4 |

OTHER PUBLICATIONS

Malinow, et al, 1989,; Circulation 1180–1188.*
Alberts et al. (Molecular Biology of the Cell, 3rd edition, 1994, p. 465).*
Freshney (Culture of Animal Cells, A Manual of Basic Techniques, Alan R. Liss, Inc., 1983, New York, p4).*
Dermer (Bio/Technology, 1994, 12:320).*
Tockman et al. (Cancer Res., 1992, 52:2711s–2718s).*
Vallance, P., et al., "Accumulation of an endogenous inhibitor of nitric oxide synthesis in chronic renal failure," *The Lancet*, 339: pp. 572–75 (Mar. 1992).
Roberts, J. M., et al., "Pre–eclampsia: more than pregnancy–induced hypertension," *The Lancet*, 341: pp. 1447–1451 (Jun. 1993).
Del Vecchio, S., et al., "Human Urolkinase Receptor Concentration in Malignant and Benign Breast Tumors by in Vitro Quantitative Autoradiography: Comparison with Urokinase Levels," *Cancer Research*, 53: pp. 3198–3206 (Jul. 1993).
Fickling, S. A., et al., "Plasma concentrations of endogenous inhibitor of nitric oxide synthesis in normal pregnancy and pre–eclampsia," *The Lancet*, 342: pp. 242–243 (Jul. 1993).

Lord, E. M., et al., "Detection o Hypoxic Cells by Monoclonal Antibody Recognizing 2–Nitroimidazole Adducts," *Cancer Research*, 53: pp. 5721–5726 (Dec. 1993).
Klokker, M., et al., "Influence of in vivo hypobaric hypoxia on function of lymphocytes, neutrocytes, natural killer cells, and cytokines," *J. Appl. Physiol.*, 74(3): pp. 1100–1106 (1993).
Zhou, Y., et al., "Increased depth of trophoblast invasion after chronic constriction of the lower aorta in rhesus monkeys," *Am. J. Obstet. Gynecol.*, 169: pp. 224–229 (1993).
Pahl, H. L., et al., "Oxygen and the Control of Gene Expression," *BioEssays*, 16(7): pp. 497–502 (Jul. 1994).
Foekens, J. A., et al., "Plasminogen Activator Inhibitor–1 and Prognosis in Primary Breast Cancer," *Journal of Clinical Oncology.*, 12(8): pp. 1648–1658 (Aug. 1994).
Pedersen, H., et al., "Prognostic Impact of Urokinase, Urokinase Receptor, and Type 1 Plasminogen Activator Inhibitor in Squamous and Large Cell Lung Cancer Tissue," *Cancer Research*, 54: pp. 4671–4675 (Sep. 1994).
Sawa, H., et al., "Increased Intramural Expression of Plasminogen Activator Inhibitor Type 1 After Balloon Injury: A Potential Progenitor of Restenosis," *Journal of the American College of Cardiology*, 24(7): pp. 1742–1748 (Dec. 1994).
Arnman, V., et al., "Expression of Plasminogen Activator Inhibitor–1 mRNA in Healthy, Atherosclerotic and Thrombotic Human Arteries and Veins," *Thrombosis Research*, 76(5): pp. 487–499 (1994).
Salat, C., et al., "Parameters of the fibrinolytic system in patients undergoing BMT: elevation of PAI–1 in veno–occlusive disease," *Bone Marrow Transplantation*, 14: pp. 747–750 (1994).
Shweiki, D., et al., "Induction of vascular endothelial growth factor expression by hypoxia and by glucose deficiency in multicell spheroids: Implications for tumor angiogenesis," *Proc. Natl. Acad. Sci. U.S.A.*, 92: pp. 768–772 (Jan. 1995).
Grøndahl–Hansen, J., et al., "Prognostic Significance of the Receptor for Urokinase Plasminogen Activator in Breast Cancer," *Clinical Cancer Research*, 1: pp. 1079–1087 (Oct. 1995).
Rutherford, R. A. D., et al., "Nitric oxide synthase in human placenta and umbilical cord from normal, intrauterine growth–retarded and pre–eclamptic pregnancies," *British Journal of Pharmacology*, 116: pp. 3099–3109 (1995).

(List continued on next page.)

Primary Examiner—Anthony C. Caputa
Assistant Examiner—Gary B Nickol
(74) *Attorney, Agent, or Firm*—Licata & Tyrrell P.C.

(57) ABSTRACT

A method for diagnosing hypoxia, endothelial dysfunction, a vascular or circulatory condition of a subject, in which the level of expression of a gene, and/or the level of a metabolite or metabolic by-product in a biological test sample is measured and compared to a control sample so as to assess the vascular condition of the subject, is described.

15 Claims, 26 Drawing Sheets

OTHER PUBLICATIONS

Genbacev, O., et al., "Hypoxia Alters Early Gestation Human Cytotrophoblast Differentiation/Invasion In Vitro and Models the Placental Defects that Occur in Preeclampsia," *J. Clin. Invest.*, 97(2): pp. 540–550 (Jan. 1996).

Costantini, V., et al., "Combined Overexpression of Urokinase, Urokinase Receptor, and Plasminogen Activator Inhibitor–1 Is Associated with Breast Cancer Progression," *Cancer*, 77(6): pp. 1079–1088 (Mar. 1996).

Bunn, H. F. and Poyton, R. O., "Oxygen Sensing and Molecular Adaptation in Hypoxia," *Physiological Review*, 76(3): pp. 839–840 and 858–885 (Jul. 1996).

Kokame, K. et al., "Homocystein–respondent Genes in Vascular Endothelial Cells Identified by Differential Display Analysis," *Journal of Biological Chemistry*, 271(47): pp. 29659–65 (Nov. 1996).

Acker, H., "PO2 Affinities, Heme Proteins, and Reactive Oxygen Intermediates Involved in Intracellular Signal Cascades For Sensing Oxygen," *Adv. Exp. Med., Biol.*, 410: pp. 59–63 (1996).

Dachs, G. U. and Stratford, I. J., "The molecular response of mammalian cells to hypoxia and the pontential for exploitation in cancer therapy," *Br. J. Cancer Suppl.*, 27: pp. S126–S132 (1996).

O'Rourke, J. F., et al., "Identification of hypoxically inducible mRNAs in HeLa cells using differential–display PCR, Role of hypoxia–inducible factor–1," *Eur. J. Biochem.*, 241: pp. 403–409 (1996).

Graham, C., et al., "Hypoxia Induced Changes in Gene Expression in Human Trophoblast Cells in Vitro." *Faseb Journal*, 11(3): A257, Abstract #1491 (Apr. 6–9, 1997).

van Belzen, N., et al., "A Novel Gene Which Is Up–Regulated during Colon Epithelical Cell Differentiation and Down–Regulated in Colorectal Neoplasms," *Laboratory Investigation*, 77(1): pp. 85–92 (Jul. 1997).

Graham, C., et al., "Hypoxia stimulates expression of the urokinase receptor and invasion of extracellular matrix by trophoblast cells through a heme protein–dependent pathway." *Placenta*, 18(5–6): A24, Abstract (Sep. 13–17, 1997).

Cuvier, C., et al., "Exposure to hypoxia, glucose starvation and acidosis: effect on invasive capacity of murine tumor cells and correlation with cathepsin (A+B) secretion," *Clinical & Experimental Metastasis*, 15(1): pp. 19–25 (1997).

Czyzyk–Krzeska, M. F., "Molecular aspects of oxygen sensing in physiological adaptation to hypoxia," *Respiration Physiology*, 110: pp. 99–111 (1997).

Goonasekera, C. D. A. et al., "Nitric oxide synthase inhibitors and hypertension in children and adolescents," *Journal of Hypertension*, 15(8): pp. 901–909 (1997).

Hedner, T. and S. Xiangying, "Measures of Endothelial Function as an Endpoint in Hypertension?" *Blood Pressure*, 6(Suppl. 2): pp. 58–66 (1997).

Salceda, S., et al., "Complex role of protein phosphorylation in gene activation by hypoxia," *Kidney International*, 51: pp. 556–559 (1997).

Himelstein, B. P. and Koch, C. J., "Studies of type IV collagenase regulation by hypoxia," *Cancer Letter*, 124(2): Abstract (Feb. 1998).

Graham, C. H. et al., "Hypoxia stimulates expression of the urokinase receptor in human breast cancer cells." *Proceedings of the American Association for Cancer Research*, 39: p. 297, Abstract #2030 (Mar. 1998).

Fitzpatrick, T. E. and Graham, C. H., "Stimulation of plasminogen activator inhibitor–1 by hypoxia in first trimester human cytotrophoblasts," *FASEB J.*, Part 1, 12(4): A48, Abstract #280 (Apr. 18–22, 1998).

Graham, C. H. et al., "Hypoxia Stimulates Urokinase Receptor Expression through a Heme Protein–Dependent Pathway," *Blood*, 91(9): pp. 3300–3307 (May 1998).

Pinsky, D. J. et al., "Coordinated Induction of Plasminogen Activator Inhibitor–1 (PAI–1) and Inhibition of Plasminogen Activator Gene Expression by Hypoxia Promotes Pulmonary Vascular Fibrin Deposition," *Journal of Clinical Investigation*, 102(5): pp. 918–928 (Sep. 1998).

Kurdistani, S. K., et al., "Inhibition of Tumor Cell Growth by RTP/rit42 and its Responsiveness to p53 and DNA Damage," *Cancer Research*, 58: pp. 4439–4444 (Oct. 1998).

Bae, M. K., et al., "Identification of Genes Differentially Expressed by Hypoxia in Hepatocellular Carcinoma Cells," *Biochemical and Biophysical Research Communications*, 243: pp. 158–162 (1998).

Fitzpatrick, T. E. and Graham, C. H., "Stimulation of Plasminogen Activator Inhibitor–1 Expression in Immortalized Human Trophoblast Cells Cultured under Low Levels of Oxygen," *Experimental Cell Research*, 245: pp. 155–162 (1998).

Kress, S., et al., "Expression of hypoxia–inducible genes in tumor cells," *J. Cancer Res. Clin. Oncol.*, 124: pp. 315–320 (1998).

Miyata, T., et al., "Analysis of Gene Expression in Homocysteine–Injured Vascular Endothelial Cells: Demostration of GRP78/BiP Expression, Cloning and Characterization of a Novel Reducing Agent Tunicamycin Regulated Gene." *Seminars in Thrombosis and Hemostasis*, 24(3): pp. 285–291 (1998).

Nürnberger, W., et al., "Endothelial dysfunction after bone marrow transplantation: Increase of soluble thrombomdulin and PAI–1 in patients with multiple transplant–related complications," *Ann Hematol*, 76: pp. 61–65 (1998).

Pak, B. J., et al., "Differential Display Analysis of Oxygen–mediated Changes in Gene Expression in First Trimester Human Trophoblast Cells," *Placenta*, 19: pp. 483–488 (1998).

Rofstad, E. K. and Danielsen, T., "Hypoxia–induced angiogenesis and vascular endothelial growth factor secretions in human melanoma," *British Journal of Cancer*, 77(6): pp. 897–902 (1998).

van Belzen, N., et al., "Expression of differentiation–related genes in colorectal cancer: possible implications for prognosis," *Histol Histopathol*, 13: pp. 1233–1242 (1998).

Graham, C. H., et al., "Hypoxia–Mediated Stimulation Of Carcinoma Cell Invasiveness Via Upregulation Of Urokinase Receptor Expression," *Int. J. Cancer*, 80: pp. 617–623 (1999).

Ganong, W. F., "Gas Transport Between the Lung & the Tissues," *Review of Medical Physiology*. 19th Edition, pp. 635–639 (1999).

Shimono, A., et al., "N–myc–dependent repression of Nrdl, a gene identified by direct subtraction of whole mouse embryo cDNAs between wild type and N–myc mutant," *Mechanisms of Development*, 83: pp. 39–52 (1999).

* cited by examiner a: $p < 0.05$ compared with 20% $O_2$
b: $p < 0.01$ compared with 20% $O_2$
c: $p < 0.05$ compared with 4% $O_2$ time after flutamide administration (hours)

☐ control  ☐ 35 mg/kg flutamide
▨ 25 mg/kg flutamide  ▩ 50 mg/kg flutamide

*indicates p<0.05 compared to control time after administration (hours)

☐ control  *indicates p<0.05 compared to control
▨ 500 mg/kg pp-DDE  ▩ 50 mg/kg flutamide

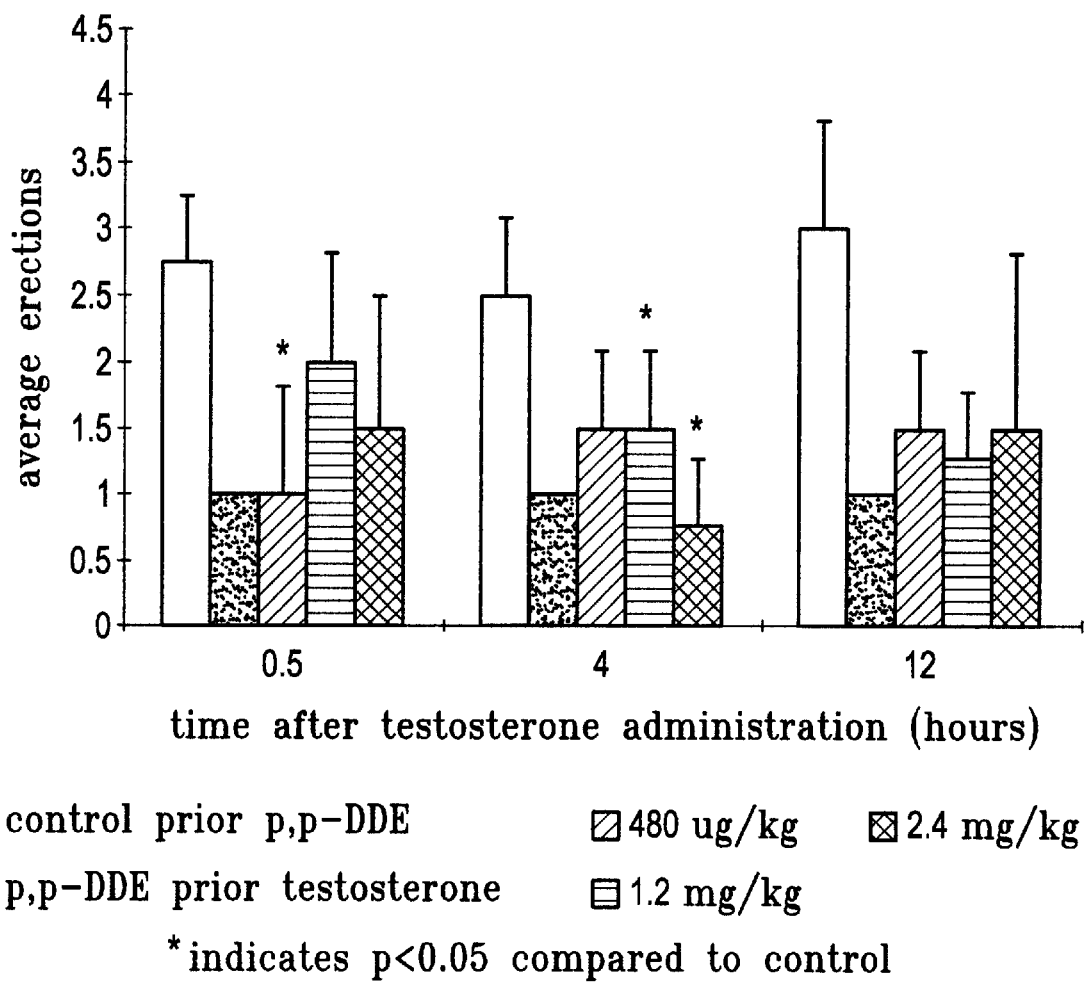

Normal chorionic villi
(Bright field)

Normal chorionic villi
(Dark field)

Preeclamptic chorionic villi
(Bright field)

Preeclamptic chorionic villi
(Dark field)

METHOD FOR DIAGNOSING A VASCULAR CONDITION

RELATED APPLICATION

This application claims the benefit of priority from U.S. application Ser. No. 60/083,763, filed May 1, 1998, now abandoned, the entire teachings of which are herein incorporated by reference.

BACKGROUND OF THE INVENTION

Many pathological conditions such as preeclampsia, peripheral vascular disease, erectile dysfunction, cancers, renal failure, heart disease, and stroke are often associated with alterations in the normal vascular condition of the affected tissues and/or systems. While the change from normal vascular condition may arise through natural physiological processes, it may also be induced transiently by perturbations such as surgical procedures, and by the presence of exogenous agents within the body. The change in vascular condition can result in a reduction in blood flow to the associated organ or system, rendering that organ or system hypoxic.

SUMMARY OF THE INVENTION

This invention relates to methods for diagnosing vascular conditions, and to methods for detecting hypoxia or endothelial dysfunction in an individual. In one aspect, the invention relates to a method for diagnosing a vascular condition leading to a hypoxic state. The methods of the invention comprise the steps of:

i) measuring the level of at least one substance in at least one biological sample, said substance having a level which is affected by a vascular condition associated with a reduction in blood flow, hypoxia or endothelial dysfunction; and ii) comparing the level of the substance in said biological sample with a standard to determine the extent of said vascular condition associated with a reduction in blood flow, hypoxia or endothelial dysfunction.

According to a further aspect of the method of the invention, a corresponding measure of the level of at least one substance is performed in at least one different biological sample, said different biological sample being unaffected by a vascular condition associated with a reduction in blood flow, hypoxia or endothelial dysfunction. The substance may be selected from the group consisting of genes, gene products, metabolites, metabolic by-products, hormones, and exogenous agents.

In a particular embodiment, the invention is a method of diagnosing a vascular condition associated with a reduction in the flow of blood within an anatomical site of an individual and the substance measured is a product of the RTP/Drg1 gene.

In additional embodiments, the invention is a method of detecting hypoxia or endothelial dysfunction in an individual and the substance measured is a product of a gene selected from the group consisting of RTP/Drg1, uPAR and PAI-1. In another embodiment, the invention is a method of detecting hypoxia or endothelial dysfunction in an individual and the substance measured is an arginine metabolite, such as L-NMMA or ADMA.

In another embodiment, the invention is a method of diagnosing a vascular condition in an individual, comprising the steps of:

i) measuring the quantity of at least two substances chosen from the group consisting of a product of the RTP/Grp1 gene, a product of the uPAR gene, a product of the PAI-1 gene and an arginine metabolite, in at least one biological sample obtained from said individual; and ii) comparing the measured quantity of said substances to a standard value for the quantity of said substances in a normal biological sample; wherein an increase in the measured quantity of at least one of said substances relative to the standard value is indicative of said vascular condition. The method of this embodiment can further comprise an indirect assay, such as evaluating the in vitro invasiveness of cells isolated from said individual.

In a further embodiment, the invention is a method of assessing an individual's risk for a vascular condition associated with a reduction in the flow of blood, comprising i) measuring the quantity of a product of the RTP/Drg1 gene in at least one biological sample; and ii) comparing the quantity of said product of the RTP/Drg1 gene in said biological sample with a standard; wherein an increase in the measured quantity of said RTP/Drg1 gene product relative to the standard value is indicative of risk for said vascular condition, and said risk correlates with the degree to which said RTP/Drg1 gene product is elevated.

The invention also relates to a method of diagnosing a vascular condition in an individual. The method comprises detecting at least one endocrine disrupter in at least one biological sample obtained from an individual, wherein the presence of said endocrine disrupter is indicative of said vascular condition. In one embodiment, the endocrine disrupter p,p-DDE is detected to diagnose erectile dysfunction.

BRIEF DESCRIPTION OF THE DRAWINGS

FIG. 24 is a graph showing APO-induced erectile response of p,p-DDE treated rats after testosterone supplementation of 480 ug/kg, 1.2 and 2.4 mg/kg tested at intervals of 0.5, 4 and 12 hours after administration (n=4).

DETAILED DESCRIPTION OF THE INVENTION

Figure 1:
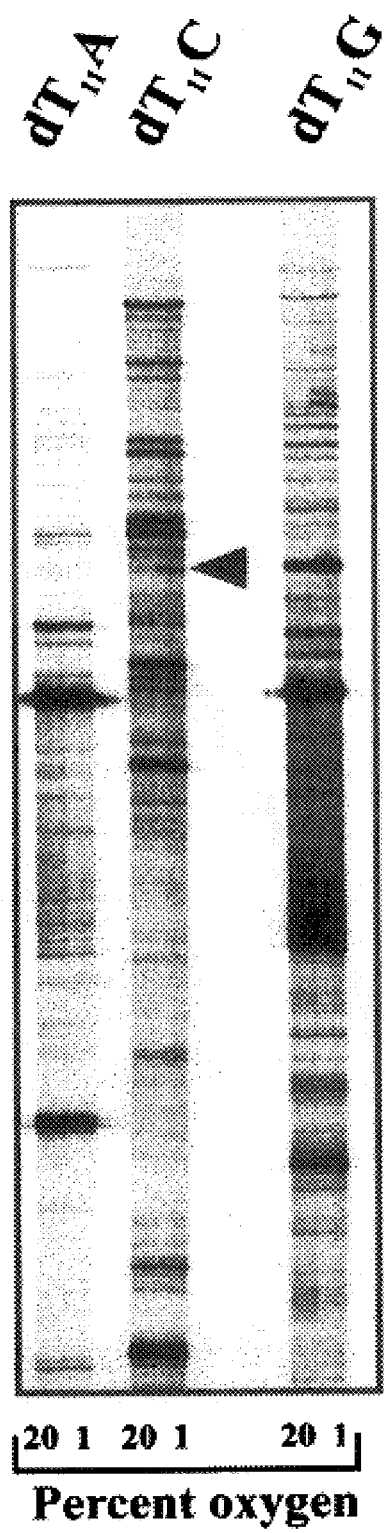
FIG. 1 is a representative autoradiogram obtained by differential display analysis of cDNA fragments generated using RNA extracted from MDA-MB-231 cells cultured under 1% or 20% oxygen. The anchor primers $dT_{11}A$, $dT_{11}C$, and $dT_{11}G$ were used, and are as indicated in the Exemplification. The band representing RTP/Drg1 is shown by an arrowhead. Only bands displaying differential intensity in at least three separate independent experiments were excised, re-amplified, and sequenced.

The vascular system is generally controlled by three classes of physiological systems: neural, humoral (hormonal), and local (e.g., at the level of endothelial cells that line the vasculature and vascular smooth muscle). The response of any one of these systems to a hypoxic state varies. Moreover, different circumstances will elicit different responses in each system. For example, endothelial cells can respond to hypoxic conditions by increasing endothelin secretion, by up-regulation of a metabolic product such as von Villebrand factor, or by increasing metabolic processes such as arginine metabolism, thereby increasing the byproducts ADMA and L-NMMA. Further, other circumstances may modify the phenotype of vascular smooth muscle cells or other cells, such that the cells alter their expression pattern of a series of factors such as urokinase-type plasminogen activator receptor (uPAR), plasminogen activator inhibitor-1 (PAI-1) and RTP/Drg1. Indeed, the up-regulated expression of various genes and their products in response to hypoxic conditions occurs in a wide range of cells, and neoplastic cells in general.

According to a broad aspect, this invention relates to methods for diagnosing hypoxia, endothelial dysfunction or a vascular condition or circulatory condition, such as a condition associated with a reduction in blood flow and/or oxygen delivery within an anatomical site or system. As used herein, the term "hypoxia" refers to a condition in which the oxygen level is reduced below the normal physiological range in a particular organism, system, organ, tissue, cell, organelle, macromolecule (e.g., protein) or molecule. The term "vascular condition" refers to the state, which can be abnormal or normal, of vascular tissue, blood flow and/or blood components. A vascular condition can result in hypoxia. However, it is appreciated that hypoxia can occur in the absence of a vascular condition (e.g., altitude sickness). Further, hypoxia can induce a vascular condition. The term "diagnosing", as used herein, encompasses monitoring, assessing, evaluating and detecting. Thus, as described herein, the invention can be used, for example, to evaluate and/or monitor a therapeutic regimen or to assess an individual's risk for a vascular condition. Typically a vascular condition to which the diagnostic methods of the invention apply is one in which the vasculature of the affected tissue or system is altered, such that blood flow to the tissue or system is reduced and the tissue or system is rendered hypoxic. Vascular, circulatory or hypoxic conditions to which the diagnostic methods of the invention apply are those associated with, but not limited to, maternal hypoxia (e.g., placental hypoxia, preeclampsia), abnormal pregnancy, peripheral vascular disease (e.g., arteriosclerosis (atherosclerosis, transplant accelerated arteriosclerosis), deep vein thrombosis), erectile dysfunction, cancers, renal failure, stroke, heart disease, sleep apnea, hypoxia during sleep, female sexual dysfunction, fetal hypoxia, smoking, anemia, hypovolemia, vascular or circulatory conditions which increase risk of metastasis or tumor progression, hemorrhage, hypertension, diabetes, vasculopathologies, surgery (e.g., per-surgical hypoxia, post-operative hypoxia), Reynaud's disease, endothelial dysfunction, regional perfusion deficits (e.g., limb, gut, renal ischemia), myocardial infarction, stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and Erythroblastosis (blue baby syndrome). In particular embodiments, the invention is a method of detecting hypoxia or endothelial dysfunction in an individual.

The method of the invention can also be used to monitor individuals receiving therapy, including prophylactic therapy, or diagnostic evaluation for a vascular condition, a hypoxic condition or a condition associated with endothelial dysfunction. For example, an individual can be monitored while recovering from surgery, while receiving antihypertensive therapy or while receiving a therapy which modifies the circulation (e.g., vascular surgery, angioplasty). An individual can also be monitored to assess the impact of various levels of exercise, such as when assessing exercise tolerance in cardiac patients (e.g., stress test). The method of the invention can also be used forensically. For example, the invention can be used to determine the time and/or cause of death as well as the extent and/or duration of hypoxia post-mortem.

In a particular embodiment, the invention relates to a method of diagnosing preeclampsia, a condition in which trophoblast cells, which under normal conditions invade the uterine wall and stimulate an increase in vasculatity necessary to support the placenta during pregnancy, are unable to stimulate an increase in vasculatity. Apparently, the invasiveness of the trophoblasts is decreased or altered. As a result, preeclampsia is characterized by an ischemic condition.

The invention also contemplates the diagnosis of altered vasculature such as reduced vascularity resulting in hypoxia within tumors. Tumor hypoxia is correlated with a poor prognosis in cancer patients, and it reduces the efficacy of treatments such as chemotherapy and radiation therapy. The invention further contemplates diagnostic applications in which a subject has chronic hypoxia or has been exposed to a transient episode of hypoxia. Such transient hypoxia may occur, for example, during surgery, as a result of administration of agents such as anaesthetics and/or a surgical procedure which transiently reduces blood flow. Hypoxia can also be a consequence of trauma. Such transient hypoxia is also one example of a condition under which potential for metastasis of cancer cells, or the degree to which cells are invasive, may be increased. Thus, the invention also relates to a method of assessing an individual's risk for metastasis.

Cellular response to a hypoxic condition resulting from altered vasculature may be characterized by any of the following, either alone or in combination: a change in the number of copies of one or more genes; a change in the level of expression of one or more genes; a change in metabolic processes and the levels of their substrates, products or by-products (i.e., metabolic indicators of a hypoxic condition). Diagnostic methods of the invention comprise subjecting one or more biological samples obtained from an individual to one or more analyses for detecting and quantifying the levels of a substance, (e.g., genes, gene products, metabolites (e.g., a substrate of a metabolic reaction), or metabolic by-products), whether the levels increase or decrease from currently accepted normal levels. In one embodiment, the substance is a cell-associated protein. A measure or measures obtained through such analyses is compared to a standard such that a vascular or hypoxic condition may be diagnosed on the basis of that comparison. In a further embodiment, the invention is a method of assessing an individual's risk for a vascular condition associated with a reduction in the flow of blood. The method comprises quantifying the levels of a substance (e.g., genes, gene products, metabolites (e.g., a substrate of a metabolic reaction), or metabolic by-products) in one or more biological samples isolated from said subject, and determining whether the levels increase or decrease from currently accepted normal levels, wherein risk correlates with the degree to which said substance, such as a RTP/Drg1 gene product, is increased or decreased from normal.

According to the invention a biological sample obtained from an individual for the purpose of analysis may be any tissue sample, cell or bodily fluid in which the substance (e.g., genes, gene products, metabolites, metabolic by-products) of interest may be present. Typical biological samples include a tissue sample such as a biopsy obtained from the organ or system under consideration, hair, blood, serum, plasma, leukocytes (e.g., T cells, B cells, NK cells, macrophages, eosinophils, basophils, monocytes), saliva, urine, breath, feces, semen, and the like. As used herein, the term "individual" refers to any living organism and includes unicellular and multicellular organisms, such as bacteria, yeasts, plants, fish, birds and mammals, such as a human.

According to the invention, genes which undergo a change in expression, such as an up-regulation of expression, in response to a hypoxic condition include, for example, genes which could mark, and in some cases have been shown to mark, the progression of hypoxic injury, progression of abnormal vascular structural changes, as well as vascular smooth muscle functions. For example these genes include, but are not limited to, the urokinase-type plasminogen activator receptor gene (uPAR), plasminogen activator inhibitor-1 gene (PAI-1), and gene RTP/Drg1 (which is also referred to as PROXY-1 (Protein Regulated by OXYgen)). In the analysis of a gene or genes, the diagnostic method of the invention involves use of suitable techniques for the identification of genes or gene products, such as the polymerase chain reaction (PCR) in combination with a probe or probes specific to the gene or genes, or a fragment thereof, to produce copies of the gene or genes in question, followed by, for example, Southern blot analysis (Southern, *J. Mol. Biol.*, 98:508 (1975)). Upon suitable analysis of the data obtained, as described below, different abundance of such a particular gene(s) or gene product(s) (e.g., mRNA, protein) in a sample (e.g., tissue sample, fluid sample), relative to the abundance of that gene(s) or gene product(s) according to a standard or from another sample known to not have a vascular or hypoxic condition, would be an indicator of hypoxia in the individual from which the test sample was taken.

The substance or substances selected can be quantified directly or indirectly using any suitable method, such as a method based upon activity (e.g., catalytic activity) or a method which measures the number of molecules of a particular substance (e.g., a specific protein, a specific mRNA molecule). When the number of molecules of a particular substance in a sample is measured, the measured value can be expressed as an absolute quantity (e.g., moles/g of sample) or relative to a reference sample.

Total cellular RNA can be isolated from a biological sample using any suitable technique, such as, for example, the single-step guanidinium-thiocyanate-phenol-chloroform method described by Chomczynski et al. (*Anal. Biochem.*, 162:156–159 (1987)). The level of an mRNA of interest is then assayed using any appropriate method, including northern blot analysis, SI nuclease mapping, polymerase chain reaction (PCR), reverse transcription in combination with the polymerase chain reaction (RT-PCR), reverse transcription in combination with ligase chain reaction (RT-LCR) and PCR or LCR in combination with hybridization. Northern blot analysis can be performed as described in Harada et al., *Cell*, 63:303–312 (1990), and S1 mapping can be performed as described in Fujita et al., *Cell* 49:357–367 (1987). Levels of mRNA encoding a protein of interest can be assayed using the RT-PCR method described in Makino et al., *Technique*, 2:295–301 (1990), using a set of oligonucleotide primers that will amplify reverse-tanscribed target mRNA. Methods for designing an appropriate set of primers are well-known in the art.

According to the invention a metabolic indicator is any compound, such as, for example, a protein, or any metabolite or metabolic by-product, the production of which is changed in response to a hypoxic condition. For example, a metabolic indicator can be a protein which is expressed by a gene which is up-regulated or down-regulated in response to hypoxia. A metabolic indicator can be, for example, a urokinase-type plasminogen activator receptor (uPAR), a plasminogen activator inhibitor-1 (PAI-1), the 43 kDa protein encoded by RTP/Drg1 (see Examples 1–3). A metabolic indicator can be a molecule (e.g., metabolite, catabolite, anabolite) the production of which is changed as a result of a vascular condition, hypoxia and/or endothelial dysfunction. For example, a metabolic indicator can be, ADMA (asymmetrical dimethyl arginine) or L-NMMA (nitric-mono-methyl arginine), which are products of abnormal arginine metabolism which can occur during hypoxia or an agent which can antagonize heme oxygenase, such as zinc-protoporphyrin. Of course, a metabolic indicator can also be any metabolite or derivative of these compounds, or any combination thereof. A metabolic indicator can also be any compound which, when present in the biological sample, has an effect on vascular function and hence blood flow. Such metabolic indicators therefore also include, for example, externally derived toxins and contaminants. An analysis for a metabolic indicator can be any suitable assay such as RIA or other methods well known in the art, such as, for example, ELISA or the dipstick test. Subject to appropriate data analysis, as discussed below, a difference in the level of the indicator or indicators in the sample under analysis indicates the presence of a vascular and/or hypoxic condition.

In addition, any indirect method for assessing whether a tissue sample has been subjected to hypoxia can also be employed, such as assessing cells for altered cell adhesion (see Example 2) and cellular invasion assays (Examples 4 and 5). For Example, in one embodiment, the invention is a method for detecting hypoxia in an individual, comprising isolating cells from said individual and evaluating the invasiveness of said cell in an in vitro assay as described herein. In this embodiment, an increase in invasiveness indicates that the individual has experienced hypoxia. In another embodiment, an in vitro cellular invasion assay can be used to assess an individuals risk for metastasis. In this embodiment, increased invasiveness indicates an increased risk for metastasis. It is preferred that the biological sample analyzed for assessing the risk for metastasis does not contain cancerous cells.

Protein levels in biological samples can be assayed using any suitable method known in the art. For example, when a protein is an enzyme, the protein can be quantified based upon its catalytic activity or based upon the number of molecules of the protein contained in a sample. Antibody-based techniques may be employed, such as, for example, immunohistological and immunohistochemical methods for measuring the level of a protein of interest in a tissue sample. For example, specific recognition is provided by a primary antibody (polyclonal or monoclonal) and a secondary detection system is used to detect presence (or binding) of the primary antibody. Detectable labels can be conjugated to the secondary antibody, such as a fluorescent label, a radiolabel, or an enzyme (e.g., alkaline phosphatase, horseradish peroxidase) which produces a quantifiable, e.g. colored, product. In another suitable method, the primary antibody itself can be detectably labeled. As a result, immunohistological labeling of a tissue section is provided. In one embodiment, an extract is produced from a biological sample (e.g., tissue, cells) for analysis. Such an extract (e.g., a detergent extract) can be subjected to western-blot or dot/slot assay of the level of the protein of interest, using routine immunoblotting methods (Jalkanen et al., *J. Cell. Biol.*, 101:976–985 (1985); Jalkanen et al., *J. Cell. Biol.*, 105:3087–3096 (1987)).

Other useful antibody-based methods include immunoassays, such as the enzyme-linked immunosorbent assay (ELISA) and the radioimmunoassay (RIA). For example, a protein-specific monoclonal antibody, can be used both as an immunoadsorbent and as an enzyme-labelled probe to detect and quantify protein of interest. The amount of such protein present in a sample can be calculated by reference to the amount present in a standard preparation using a linear regression computer algorithm (see Iacobilli et al., *Breast Cancer Research and Treatment*, 11:19–30 (1988)). In another embodiment, two different monoclonal antibodies to the protein of interest can be employed, one as the immunoadsorbent and the other as an enzyme-labelled probe.

It is appreciated that some substances which are suitable indicators of hypoxia and/or a vascular condition are not found in all biological samples. Thus, the substance or substances to be measured will be selected based upon the nature of the biological sample. For example, when the biological sample is a tissue biopsy the substance to be measured can be a gene product which is expressed in the tissue at different levels under normoxic and hypoxic condition. In a preferred embodiment, a substance which can be detected in a wide variety of biological samples is selected for analysis. When such a substance is selected, a plurality of distinct biological samples can be analyzed in a single assay. A preferred substance which can be detected in a wide variety of biological samples is a product (e.g., mRNA, protein) of the RTP/Drg1 gene. Substances which are expressed in particular tissues or cells and substances which can be detected in a variety of samples can be identified using suitable methods, such as the methods described herein.

For example, genes which are differentially expressed under normoxic and hypoxic conditions can be identified by differential display RT-PCR. The genes can then be isolated and expression patterns can be determined using conventional techniques. If desired, an antibody (e.g., anti-sera, monoclonal antibody) can be raise against a purified, recombinant or synthetic protein or fragment thereof and used to assess the tissue distribution of the protein (see Example 3).

The contents of Maniatis, T., et al., *Molecular Cloning: Laboratory Manual*, Cold Spring Harbor Laboratory, Cold Spring Harbor, N.Y. (1982), and Sambrook, J. et al., *Molecular Cloning: A Laboratory Manual*, Cold Spring Harbor Laboratory, Cold Spring Harbor, N.Y. (1989), as well as all references cited herein are hereby incorporated by reference.

According to the invention, a standard against which the above measure or measures from test samples are compared may be data obtained from a data bank corresponding to currently accepted normal levels of the genes, gene products, metabolites, and metabolic by-products under analysis. In situations such as those where standard data is not available, the methods of the invention can further comprise conducting corresponding analyses in a second set of one or more biological samples known not to have been exposed to hypoxia. Such additional biological samples can be obtained, for example, from the individual under consideration prior to the onset of a vascular or hypoxic condition, or from unaffected members of the public, or, in the case of an investigation of a localized site within an individual, from an unaffected site within said individual.

According to the methods of the invention, the comparison of the above measure or measures can be a straight-forward comparison, such as a ratio, or it can involve weighting of one or more of the measures, relative to, for example, their importance to the particular situation under consideration. The comparison can also involve subjecting the measurement data to any appropriate statistical analysis. It is important to note that in the diagnostic procedures of the invention, one or more biological samples obtained from an individual can be subjected to a battery of analyses in which a desired number of genes, gene products, metabolites, and metabolic by-products are sought to be quantified. In any such diagnostic procedure it is possible that one or more of the measures obtained will render an inconclusive result; accordingly, data obtained from a battery of measures can provide for a more conclusive diagnosis. It is for this reason that an interpretation of the data based on an appropriate weighting scheme and/or statistical analysis is desirable.

It should be noted that the diagnostic methods of the invention are not limited to the detection of endogenously-derived substances. Exogenous agents present in the body may function to disrupt physiological processes and produce conditions which resemble or result in hypoxia. For example, cobalt and nickel, obtained from compounds such as cobalt chloride and nickel chloride, can mimic hypoxic conditions which result from deficient blood flow by virtue of the fact that they can disrupt oxygen-sensing heme proteins. Thus, although a pathological condition caused by cobalt- or nickel-mediated disruption of an oxygen-sensing heme protein may not be directly caused by an abnormal or altered vascular condition, the deleterious symptoms resulting from such binding are analogous to those produced by hypoxia resulting from deficient blood flow. In addition to cobalt and nickel, other exogenous agents may similarly bind to heme, such as, for example, iron, ruthenium, rhodium, palladium, osmium, iridium, and platinum. These agents may be environmental contaminants obtained by ingestion and which bioaccumulate within the body, such as in fat deposits. Known heme proteins include globins and cytochromes. The diagnostic methods of the invention are therefore useful for detecting the presence of such exogenous agents.

Other exogenous agents may bioaccumulate within the body and disrupt physiological processes that directly affect vascular condition. For example, there are those substances which act to modify systems such as, for example, endocrine systems. An example of such an endocrine disruptor substance is a DDT metabolite such as p,p-DDE. DDT is an environmental contaminant which is particularly common in third world countries. There are, of course, a host of other compounds which act as anti-androgenics or as anti-estrogenics. In the case of p,p-DDE, a measure of the level of testosterone in an individual who has a body burden of p,p-DDE may reveal that the individual has normal levels of testosterone; however, because of the body burden of p,p-DDE, there is a subtle blockade of the actions of testosterone. The individual would therefore appear normal with respect to testosterone levels, but would in fact be sub-androgenic in terms of the required amount of testosterone for normal function. Male erectile dysfunction is an example of a vascular disorder that is known to be related to a sub-androgenic condition. Thus, using the diagnostic methods of the invention, one can determine, for example, a ratio of testosterone levels to anti-androgen levels within the body to determine whether an individual has the potential for an environmentally-induced vascular disorders such as erectile dysfunction.

Exemplification

Materials and Methods

Cells. Human MDA-MB-231 breast cancer cells were cultured in RPMI 1640 medium (Gibco BRL, Grand Island, N.Y.) supplemented with 5% fetal bovine serum (FBS; Gibco BRL). These cells were initially isolated from a single pleural effusion obtained from a 51-year old woman in 1973 (Cailleau, R., et al., *J. Natl. Cancer Inst.* 53:661–674 (1974)). HTR-8/SVneo cells were obtained from explant cultures of human first trimester placenta and immortalized by transfection with a cDNA construct containing the SVneo large T antigen as described (Graham, C. H., et al., *Exp. Cell Res.* 206:204–211 (1993)). These cells have been previously characterized and have been maintained in culture for over 120 passages in RPMI 1640 medium supplemented with 5% FBS. They exhibit a high proliferation index and share various phenotypic similarities with the non-transfected parent HTR-8 cells such as in vitro invasive ability and lack of tumorigenicity in nude mice (Graham, C. H., et al., *Exp. Cell Res.* 206:204–211 (1993)). Tumorigenic, but non-metastatic, human breast cancer MCF10A1T3B cells were provided by Dr. Bruce Elliot, Queen's University, Kingston, ON. These cells were obtained following injection of the H-ras-transformed non-tumorigenic MCF10A1 breast epithelial cells into nude mice and were maintained in DMEM/F12 supplemented with 5% FBS, 10 $\mu$g/mL insulin, 0.2 ng/mL epidermal growth factor, and 0.5 $\mu$g/mL hydrocortisone. Human aortic smooth muscle cells (HASMC) were a kind gift of Dr. Keith McCrae, Case Western Reserve University, Cleveland, Ohio. They were cultured in M199 medium (Gibco BRL) supplemented with 10% FBS.

Culture Conditions. For culture under hypoxic conditions, cells were placed in airtight chambers (BellCo Biotechnology, Vineland, N.J.) which were flushed with a 5% carbon dioxide/95% nitrogen mixture until the oxygen concentration, measured with a Miniox 1 oxygen analyzer (Catalyst Research Corp., Owings Mills, Md.), was 0%. The cells were incubated within the sealed chambers for up to 60 h at 37° C. Under these conditions, the oxygen concentration equilibrates within 1–2 h and remained at approximately 1% throughout the entire incubation period. At these levels, the $pO_2$ values reach 10–15 mmHg at the bottom of the tissue culture plate as determined with a transcutaneous $pO_2$ analyzer (Kontron Scientific Ltd., Mississauga, ON). For culture Gunder 2–10% oxygen, cells were incubated for 24 h at 37° C. in a multigas (nitrogen-carbon dioxide) incubator (Forma Scientific, Marietta, Ohio) previously allowed to equilibrate at 2–10% oxygen, 5% carbon dioxide, balance nitrogen. Control cultures were incubated at 20% oxygen/5% carbon dioxide, for 24 h, in a Sanyo carbon dioxide incubator (Esbe Scientific, Markham, ON).

To determine whether hypoxia regulates the expression of certain genes (e.g., PAI-1, uPAR, RTP/Drg1) via an iron-containing heme protein, cells were cultured for up to 72 h at 20% oxygen in the presence or absence of either 100 $\mu$M cobalt chloride, or 30 mM sodium 4,5-dihydroxybenzene-1,3-disulfonate (Tiron), or 100 $\mu$M desferrioxamine mesylate (DFO) (Sigma Chemical CO., St. Louis, Mo.). Further confirmation of the role of a heme protein in hypoxic responses can be achieved by culturing cells under hypoxia in the presence of carbon monoxide, which maintains the heme protein in the oxy state and thereby blocks heme protein-mediated hypoxic responses. Thus, cells were also cultured for 24 h at 37° C. under hypoxic conditions in the presence of 30% carbon monoxide.

Determination of Cell Viability. As an indirect measure of cell viability, lactate dehydrogenase (LDH) levels were assessed in the culture medium of HTR-8/SVneo and MDA-MB-231 cells incubated in triplicate plates under 20% oxygen or 1% oxygen for up to 72 h, using a kit from Sigma Diagnostics (St. Louis, Mo.). This assay is based on a colorimetric reaction which involves the reduction or pyruvate to lactate at a rate proportional to the amount of LDH present.

RNA Extraction and mRNA Differential Display. Total RNA was extracted from HTR-8/SVneo and MDA-MB-231 cells cultured under either standard (20% oxygen) or hypoxic (1% oxygen) conditions by the acid guanidium phenol-chloroform method (Chomczynski, P. and Sacchi, N. *Analyt.Biochem.* 162:156–159 (1987)). The RNA was then treated with ribonuclease-free deoxyribonuclease I (Promega Corp., Madison, Wis.) to remove contaminating genomic DNA and quantified spectrophotometrically. Differential display was performed according to the method of Liang and Pardee (Liang, P. and Pardee, A. B. *Science* 257:967–971 (1992)) using an RNAImage kit (GenHunter, Brookline, Mass.) as described (Pak, B. J., et al., *Placenta* 19:483–488 (1998)). Briefly, reverse transcription was performed on 0.2 $\mu$g of total RNA at 37° C. using MMLV reverse transcriptase and one of three different single-base anchored oligo-dT primers (H-$T_{11}$A, H-$T_{11}$C, and H-$T_{11}$G). The resulting cDNA was then subjected to PCR amplification, in the presence of [$^{33}$P]dATP (Dupont NEN, Markham, ON), using the same anchored primers in combination with one of eight degenerate oligonucleotide primers (HAP-1-8). PCR parameters were as follows: 94° C., 30 sec; 40° C., 2 min; 72° C., 30 sec for 40 cycles, then 72° C. for 7 min. cDNA products obtained were separated by electropheresis through 6% polyacrylamide-8M urea sequencing gels. The gels were vacuum-dried onto blotting paper, and autoradiographed for 1–3 days on Dupont Reflection NEF X-ray film (Dupont Canada, Inc., Mississauga, ON). Bands displaying differential intensities were excised, re-amplified using the above PCR conditions, and cloned into pCR2.1 or pCRII vectors (Invitrogen, San Diego, Calif.). The nucleotide sequence of the subcloned PCR fragments was determined by the dideoxynucleotide sequencing method at the Core Facility for Protein/DNA Chemistry (Queen's University, Kingston, ON). Comparison of DNA homology with the GenBank database was performed using the BLAST 2.0 algorithm (blastn with default parameters, Altschul, S. F., et al., *Nucleic Acids Res* 25(17):3389–3402 (1997)).

Northern Blot Analysis. Total RNA was isolated from cell lines as described above. Aliquots of 20 $\mu$g were denatured and subjected to electrophoresis in 1% agarose-formaldehyde gels (Sambrook, J., Fritsch, E. F., and Maniatis, T. *Molecular Cloning: A Laboratory Manual*, Cold Spring Harbor Laboratory, Cold Spring Harbor, N.Y. (1989)). RNA was transferred to nylon membranes (Micron Separations, Inc., Westboro, Mass.). After prehybridization at 42° C. for 2–3 h in 50% formamide, 5×Denhardt's solution, 0.5% sodium dodecyl sulfate (SDS), 6×SSC (1×SSC: 0.15M NaCl, 15 mM sodium citrate, pH 7.0), and 100 $\mu$g/mL denatured salmon sperm DNA, membranes were hybridized for a period of time of overnight (~18 h) to about 72 h at 42° C. with a cDNA probe (e.g., RTP/Drg1, PAI-1 (PAI-1 cDNA provided by Dr. Keith McCrae, Temple University School of Medicine, Philadelphia, Pa.), uPAR (Higazi A, et al., *J Biol Chem* 266:12752, (1995)) prelabeled with [$^{32}$P]-dCTP using a Pharmacia Oligolabelling kit (Pharmacia Biotech, Piscataway, N.J.). The hybridization solution contained 6×SSC, 0.5% SDS, 100 µg/mL denatured salmon sperm DNA, 50% formamide and cDNA probe. After hybridization, the membranes were washed with 2×SSC and 0.5% SDS at room temperature for 15 min, 2×SSC and 0.1% SDS at room temperature for 15 min, and 0.1×SSC and 0.5% SDS for 30 min. Dupont Reflection NEF film (Dupont Canada, Inc., Mississauga, ON) was exposed to the membranes for 1–3 days at −80° C. Bands on radiographic film were analyzed using a SigmaGel gel analysis software package (Jandel Scientific Software, San Rafael, Calif.).

Determination of PAI-1 Levels in the Culture Medium. The levels of PAI-1 in the conditioned medium of HTR-8/SVneo cells cultured under standard or hypoxic conditions for 8, 12 and 24 hours were measured and compared using a specific PAI-1 ELISA kit (American Diagnostica, Greenwich, Conn.), which detects latent and active forms of PAI-1 and PAI-1 complexes.

Cell Adhesion Assay. Wells in 96-well tissue culture plates were coated with 100 µl of 10 µg/ml of vitronectin or 10 µg/ml of BSA in PBS and left to bind to the plastic surface overnight at 4° C. Following 2–3 gentle washes with PBS, the wells were blocked with 100 µl of 1 mg/ml BSA in RPMI medium for 1–2 hours at 37° C. During this time, the cells were harvested with 5 mM EDTA in PBS at 4° C., washed once or twice in cold BSA/RPMI medium and adjusted to a concentration of 5×10$^5$ cells/ml. One hundred microliters of the cell suspension were then added to each well and the cells were allowed to adhere for 45 minutes at 37° C. under either standard (20% $O_2$) or hypoxic (1% $O_2$) conditions. The wells were washed gently with warm PBS 3 or 4 times to remove unbound cells, each time inverting the plates and shaking them until the BSA control wells were almost clear of cells. The remaining cells were fixed with 4% paraformaldehyde in PBS for 1–2 hours and stained with 1% toluidine blue in 1% sodium borate for 2 hours. Finally, excess stain was removed with distilled water, the plates were allowed to dry and their absorbance was read at 570 nm using a Dynatech MR4000 plate reader (Dynatech Laboratories Inc., Chantilly, Va.).

Three-Dimensional Multicellular Aggregates. Multicellular aggregates were generated as described (Graham, C. H., et al., *J.Natl.Cancer Inst.* 86:975–982 (1994); Kobayashi, H., et al., *Proc.Natl.Acad.Sci. USA* 90:3294–3298 (1993)). Briefly, each well of 24-well plates was coated with 0.25 mL of melted 1% sea-plaque agarose in serum-free medium. After the agarose solidified, 1×10$^5$ cells in 1 mL of complete medium were plated in each well and incubated at 37° C., 5% carbon dioxide, for 3–5 days to allow for aggregate formation. Under these conditions, the cells could not attach to the tissue culture plates and single multicellular aggregates of approximately 0.5 mm in diameter were evident at the end of the incubation period.

Production of Anti-Drg1 Antiserum. After transfection of *E. coli* with an almost full-length (first two codons lacking) Drg1 cDNA cloned into the pProEXHT expression vector, fusion protein was harvested from bacterial lysates by affinity chromatography with Ni-NTA agarose (Qiagen), followed by denaturing batch purification (Qiagen) according to the manufacturer's protocol. Immunization of rabbits was performed by repeated intradermal injection of 100 µg of the DRG1 fusion protein with (in)complete Freund's adjuvant (Eurogentech). Specificity of the antiserum was assessed by Western blotting and immunohistochemistry. In Western blots, using protein isolated from HT29 and Caco2 colon cancer cells, as well as proteins extracted from *E. coli* cells transfected with the Drg1 construct or the empty vector, specificity was confirmed by the occurrence of a 43-kDa (Caco2 and HT29 cells) or a 53.5-kDa (recombinant) band, the latter lacking in empty vector-transfected *E. coli*. Immunoreactivity on tissue sections was abolished by preincubation of the antiserum with purified recombinant Drg1 protein.

Western Blot Analysis. To examine levels of RTP/Drg1 protein, cells were lysed with buffer containing 40 mM HEPES pH 7.2, 100 mM NaCl, 20% glycerol, 0.1 mM EDTA pH 8.0, 0.2% Triton X-100 (polyoxyethylene (10) isooctylphenyl ether), 1 mM DTT, and 2 mM PMSF, and centrifuged briefly at 4° C. The supernatants were collected and stored at −80° C. until use. SDS-PAGE was performed and resolved proteins were transferred to Immobilon-P membranes (Millipore Corp., Bedford, Mass.) using a semi-dry transfer cell (Bio-Rad Laboratories, Mississauga, ON). Membranes were blocked by incubation overnight at 4° C. in a PBS-buffered solution containing 0.01% Tween 20 (polyoxyethylene(20) sorbitan monolaurate) (PBS-T) and 5% casein. The blots were then incubated with polyclonal rabbit anti-Drg1 antiserum followed by incubation with a peroxidase labeled goat anti-rabbit IgG secondary antibody (Vector Lab. Inc., Burlingame, Calif.). Antigen was detected by enhanced chemiluminescence (ECL, Amersham Canada Inc., Oakville, ON) and exposure of the membrane onto Dupont Reflection NEF film (Dupont Canada, Inc., Mississauga ON).

Immunohistochemistry. RTP/Drg1 protein in sections of HTR-8/SVneo and MDA-MB-231 multicellular aggregates was localized by immunohistochemistry using the avidin-biotin peroxidase method (Hsu, S. M., et al., *J.Histochem.Cytochem.* 29:577–580 (1981)). Tissue blocks fixed in paraffin were cut into 4-µm-thick sections, deparaffinized, and immersed in 0.3% hydrogen peroxide in methanol for 30 min to abolish endogenous peroxidase activity. The sections were blocked with 10% normal goat serum (NGS) for 20 min to reduce nonspecific staining. Anti-Drg1 antiserum diluted with 2% NGS (1:500) was applied to the sections and incubated overnight at 4° C. This was followed by incubation with a 1:200 dilution of a biotinylated goat anti-rabbit IgG (Vector Laboratories, Burlingame, Calif.) for 30 min at room temperature and a subsequent 30 min incubation with Vectastain ABC reagent (Vector Laboratories). Antigenic sites were localized by incubation with diaminobenzidine solution and hydrogen peroxide for 5 min. Sections were counterstained with Gill's No.2 hematoxylin, dehydrated, and mounted. Negative controls consisted of sections incubated with preimmune serum used at the same concentration as the anti-Drg1 antiserum.

Determination of uPAR expression by flow cytometry. For flow cytometry, cells were released from flasks by incubation in cold PBS containing 5 mM EDTA. One million cells were then incubated for 1 h, at 4° C., with either 10 µg/ml of mAb 3937, or control mouse IgG$_{2a}$, used at the same concentration. Bound antibody was detected using FITC-conjugated goat anti-mouse immunoglobulin. Cells were then fixed with 2% paraformaldehyde in PBS prior to analysis using a Coulter Elite Flow Cytometer.

Determination of uPAR expression by urokinase binding analysis. Measurement of uPAR expression by ligand binding analysis was performed using [$^{125}$I]-prourokinase as the ligand, as described (Zini J M, et al., *Blood* 79:2917 (1992)). Prourokinase was radiolabeled with $^{125}$I, using Iodobeads, to a specific radioactivity of at least 10$^6$ cpm/µg. Cells were then chilled to 4° C., washed with cold PBS containing 1% BSA, and incubated for 2 h with increasing concentrations of [$^{125}$I]-prourokinase in the absence (to determine total binding) or presence (to determine non-specific binding) of a 100-fold molar excess of unlabeled prourokinase. Specific binding was defined as the difference between total and non-specific binding, and analyzed by non-linear curve fitting methods (least squares method) using the Kaliedograph software program (Synergy Software, Reading, Pa.).

In vitro invasion assay. An assay which employs reconstituted basement membrane (Matrigel; Collaborative Biomedical Products, Bedford, Mass.) as the substrate for invasion was used to determine the effect of hypoxia on the invasiveness of tumor cells. Costar Transwell inserts (6.5 mm diameter polycarbonate membrane, 8 $\mu$m pore; Corning Costar Corp., Cambridge, Mass.) were coated with 100 $\mu$l of a 1 mg/ml solution of Matrigel diluted in cold serum-free culture medium, placed in the wells of a 24-well tissue culture plate and allowed to air-dry for 12 h in a laminar flow cabinet. After reconstituting the Matrigel by incubating for 1 h with 100 $\mu$l of serum-free medium, $5.0 \times 10^4$ cells in 100 $\mu$l aliquots of serum-containing medium were added to the Transwells. Following a 24-h incubation under either 20% or 1% $O_2$ in the absence or presence of 10 $\mu$g/ml blocking anti-uPAR antibody (3936), or under 1% $O_2$+30% CO (to assess the role of a heme protein on invasion), cells on the surface of the Matrigel-coated polycarbonate membrane (non-invading cells) were removed by scraping with a cotton swab. Cells which invaded through the Matrigel and the pores of the underlying membrane were fixed for 10 min in Carnoy's fixative (25% acetic acid, 75% methanol) and stained for 3 h in 1% toluidine blue, 1% sodium borate. Following several washes in tap water, the membranes were removed with a small scalpel blade, placed on a microscope slide and coverslipped. The invasion index' was then determined by counting, under a microscope, the total number of stained cells in the underside of the polycarbonate membranes. In a pilot study, it was determined that the rate of MDA-MB-231 cell proliferation is similar at 1% vs. 20% $O_2$ for at least 48 h, thereby indicating that differences in cell numbers on the membranes at the end of the invasion assay are reflective of altered invasive ability alone.

Alternatively, cells (e.g., HTR-8/SVneo, MDA-MB-231) were labeled by incubation for 24 h in the presence of 10 $\mu$Ci/ml [$^3$H]-thymidine. The cells were then harvested, adjusted to a concentration of $5.0 \times 10^5$/ml, and 100 $\mu$l aliquots added in triplicate to the upper wells of the invasion chambers. After a 24-h incubation, cells in the upper and lower compartments of the chambers were harvested. The invasion index, reflecting the percentage of added cells which had invaded the Matrigel was determined by measurement of the radioactivity in the upper and lower compartments, as well as in the membrane.

Determination of PA and gelatinase levels in the culture medium. Concentrations of gelatinase and plasminogen activators in the conditioned medium of HTR-8/SVneo cells cultured under standard or hypoxic conditions were compared using gel zymography, as described (Graham C H, et al., *Exp Cell Res* 206:204 (1993)). The concentrations of uPA antigen in these samples were more accurately measured using a specific uPA ELISA.

Determination of cell surface PA activity. Cell surface plasminogen activator (PA) activity was determined using a modification of the fluorometric assay of Ellis et al. *J Biol Chem* 266:12752 (1991). Briefly, HTR-8/SVneo cells were plated in quadruplicate wells of a 96-well tissue culture plate, and allowed to grow to 95% confluency. Following a 24 h incubation under an atmosphere of either 20% $O_2$ or 1% $O_2$, the cells were washed twice, and further incubated with fresh medium containing plasminogen and the plasmin peptide substrate, HDVLL-AMC, used at concentrations of 0.2 $\mu$M and 0.5 mM, respectively. Plasmin generation was assessed by determining the fluorescence within individual microplate wells 30 min later, using a Perkin Elmer LS50B Luminescence Spectrophotometer (excitation wavelength 360 nm, emission wavelength 460 nm).

Zymographic analysis of secreted and cell-associated plasminogen activators. To examine the levels of secreted plasminogen activators, serum-free media (EX-CELL 300 medium, JRH Biosciences, Lenexa, Kans.) conditioned by subconfluent cultures in 35-mm plates incubated under 20% or 1% $O_2$ for 8, 12, and 24 h were collected and stored at minus 80° C. After thawing on ice, volumes containing 200 ng of protein were mixed with SDS sample buffer and loaded into the wells of an SDS/polyacrylamide gel containing 2 mg/ml α-casein and 0.025 units/ml of plasminogen (Sigma). As a control, parallel samples were loaded onto gels lacking plasminogen. Following electrophoresis, the gels were washed twice for 15 min in 2.5% Triton X-100 (Sigma) in water, rinsed briefly with water and incubated overnight in a solution of 50 mM TRIS and 5 mM $CaCl_2$. To specifically determine the levels of uPA in the conditioned media, gels were incubated overnight with 100 mM amiloride in 50 mM TRIS, 5 mM $CaCl_2$. Amiloride selectively inhibits uPA but not other plasminogen activators (Vassalli and Belin, *FEBS Lett.*, 214:187–191 (1987)). After incubation, gels were stained with 0.4% Coomassie brilliant blue R-250 in 10% acetic acid/40% methanol and destained in 10% acetic acid/40% methanol. Gels were dried between sheets of cellophane on a Savant gel drier (Savant Instruments, Inc., Farmingdale, N.Y.).

To assess the levels of plasminogen activators associated with cells cultured for 24 h under 20% and 1% $O_2$, extracts were prepared by disrupting trypsinized cell pellets with 2% SDS in Tris-buffered saline (TBS; 10 mM Tris, 0.15 M NaCl, pH 7.5) using a Polytron homogenizer (Brinkmann Instruments, Rexdale, ON, Canada). The homogenates were centrifuged at 15,000 g for 15 min to remove insoluble materials and 100 $\mu$g of extracted protein were analyzed by casein-plasminogen gel zymography as described above.

In situ Hybridization

Synthesis of cRNA probes. The plasmind pCRII (Invitrogen) was linearized by digesting two aliquots of 50 $\mu$g each for antisense and sense probes with EcoRV (Gibco BRL) and BamHI (Gibco BRL) respectively, overnight at 37° C. The DNA was quantified and brought to a concentration of 200 ng/$\mu$l. In vitro transcriptions were set up on ice with each reaction containing, in order, 1.3 $\mu$l nuclease-free water, 4.0 $\mu$l 5×transcription buffer, 2.0 $\mu$l 100 mM DTT, 0.8 $\mu$l rRNAsin (Promega), 4.0 $\mu$l GAC mixture (2.5 mM each of GTP, ATP and CTP), 2.4 $\mu$l 100 mM UTP, 1.0 $\mu$l linearized DNA, 4.0 $\mu$l [$^{35}$S]-dUTP (1 mCi/80 $\mu$l) and 0.5 $\mu$l RNA polymerase (SP6 or T7). The reactions were mixed by pipetting up and down, centrifuged for 10 sec, and incubated for 1 h at 37° C. in a water bath. Following incubation, 1 $\mu$l of RQ1 RNase-free DNase (Gibco BRL) was added, left for 15 min at 37° C. 1 $\mu$l of yeast tRNA (Gibco BRL) was added to the reaction followed by 450 $\mu$l phenol:chloroform:isoamyl alcohol (25:24:1) extraction. Reaction products were precipitated overnight at −20° C. with 45 $\mu$l 3M sodium acetate (pH 5.2) and 900 $\mu$l of ice-cold RNase-free 100% ethanol. The next day, the RNA was pelleted by centrifugation for 30 min at 14,000 rpm at 4° C., rinsed with 70% ethanol and vacuum dried. The pellet was resuspended in 500 μl 10% SDS, 0.25 M EDTA (pH 8.0) and 3M sodium acetate (pH 5.2) and precipitated overnight at −20° C. with 100% ethanol. The RNA was pelleted by centrifugation for 30 min at 14,000 rpm at 4° C. and rinsed with 70% ethanol. The pellet was resuspended with 200 μl of 20 mM DTT and RNA was subjected to limited alkaline lysis with 200 μl of 0.2 M carbonate buffer (pH 10.2) for 30 minutes at 60° C. The reaction was neutralized with 12 μl of 3M sodium acetate (pH 5.2) and 20 μl 10% glacial acetic acid. The mixture was precipitated with 100% ethanol overnight at −20° C. The final cRNA product was pelleted by centrifugation, rinsed with 70% ethanol, dissolved in 100 μl TE (pH 8.0) buffer with 20 mM DTT and stored at −80° C. until use. The quality of the riboprobes was checked by running 1 μl of final product through an 8% polyacrylamide gel and exposing the gel to film. Discrete bands indicated efficient transcription reactions. Incorporation of the radiolabel was determined by assessing counts from aliquots of 5 μl at various time points throughout the transcription reaction.

Pre-hybridization and Post-hybridization. Tissue sections were deparaffinized in xylene for 5 min, rehydrated in descending alcohols for 3 min each (100, 90 and 70%) and incubated in 0.2% Triton-X100 in PBS for 1 h at room temperature, proteinase-K (1 μg/ml) for 30 min at 37° C. and 0.25% acetic anhydride (Fisher) in triethanolamine (TEA, Sigma) buffer for 10 min at room temperature. The sections were then incubated with in situ hybridization buffer containing 0.3 M NaCl, 20 mM Tris (pH 8.0), 1 mM EDTA, 1×Denhardt's solution, 500 μg/ml yeast tRNA, 100 μg/ml denatured salmon sperm DNA, 10% dextran sulfate (Fisher), 0.1% SDS, 100 mM dithiothreital (DTT) and 50% formamide at 42° C. for 2 h. The slides were then hybridized with [$^{35}$S]-dUTP labeled antisense or sense cRNA probes at concentrations of 1×10$^6$ disintigrations/min/ml in 1×in situ hybridization buffer for 18 to 24 hours at 55° C. Glass coverslips (Fisher) were removed by incubation in 2×SSC and tissue sections were then washed in 2×SSC, 10 mM DTT at room temperature for 3 min followed by 10 min wash at 55° C. in in situ hybridization buffer. The sections were treated with RNase A (0.4 mg/ml RNase A (Sigma) in 0.5 M NaCl, 10 mM Tris (pH 8.0), 1 mM EDTA (pH 8.0)) for 30 min at 37° C.

Post-hybridization washes consisted of 2×SSC with 1M DTT for 5, 10 and 15 min each at room temperature followed by 4–30 min washes in 2×SSC with 1 M DTT at 55° C. and 2–15 min washes in 0.1×SSC at 55° C. The slides were dehydrated in ascending alcohols (70, 90 and 100% ethanol) and for estimation of exposure times, they were exposed to X-Omat AR film at −70° C. for 18–24 h. The sections were then dipped in photoemulsion (NBT-2 nuclear track emulsion, Kodak Laboratories, Rochester, N.Y.) and exposed at 4° C. for 21–30 days. The photoemulsion was developed with a D-19 developer, fixed, stained with hematoxylin and eosin, and mounted with mounting medium. The slides were viewed under a light microscope and specificity of in situ hybridization signal was demonstrated by comparing identical slides radiolabeled with sense cRNA probes.

EXAMPLE 1

Up-regulation of urokinase-type plasminogen activator receptor (uPAR) in cancer cells by hypoxia has been demonstrated in vitro (Graham, C. H., et al., *Proc. Amer. Assoc. Cancer Res.*, 39:297 (1998)). Compared with standard conditions (20% O$_2$), cells cultured for 24 hours under 1% O$_2$ exhibited a 28% increase in cell-surface uPAR protein and a 4.5-fold increase in uPAR mRNA levels, as determined by flow cytometry and Northern blot analysis. Cells cultured for 24 hours under standard conditions with 100 μM cobalt chloride also exhibited elevated uPAR protein and mRNA levels, suggesting that hypoxia stimulates uPAR expression through a heme protein. Similar effects on uPAR mRNA were obtained when tumor cells were cultured with sodium 4,5-dihydroxy-benzene-1,3-disulfonate (Tiron), an iron-chelating agent. These results suggest that hypoxia may contributed to malignant progression by stimulating uPAR expression on cancer cells.

EXAMPLE 2

In vitro studies were undertaken to determine whether hypoxia, similar to that which occurs naturally in, for example, the first trimester placenta and hypoxic tumors, affects plasminogen activator inhibitor-1 (PAI-1) expression. These studies show that hypoxia up-regulates PAI-1, high levels of which correlate with a poor prognosis in some cancer patients.

Culture Under Hypoxia for 24 Hours Does Not Affect Viability of Trophoblast Cells Before examining the effects of hypoxia on expression of PAI-1 by the HTR8/SVneo trophoblast cells, it was necessary to verify whether they could tolerate prolonged periods of low oxygen without significant effect on their viability. No detectable variations in cell morphology could be seen at the light microscopic level between cells cultured under standard conditions and those cultured under 1% oxygen for a duration of 24 hours. The viability of these cells was further assessed by measuring lactate dehydrogenase (LDH) levels in the medium collected from both culture conditions. Two independent experiments, each performed in triplicate, could not detect significant differences in LDH accumulation (Table 1). Similarly, cultures exposed to 8, 12 and 24 hours of hypoxia did not exhibit reduced cell viability as determined by trypan blue exclusion (Table 1).

TABLE 1

Assessment of cell viability as determined by lactate dehydrogenase (LDH) accumulation and trypan blue exclusion

|  |  | 20% Oxygen | 1% Oxygen | P (Student's t-Test) |
| --- | --- | --- | --- | --- |
| LDH levels (U/ml) | 24 h | 163.4 ± 7.0 | 145.6 ± 5.0 | 0.26 |
| Trypan blue exclusion | 8 h | 89.1% ± 5.0% | 87.5% ± 2.0% | 0.46 |
|  | 12 h | 85.4% ± 0.5% | 83.7% ± 5.0% | 0.80 |
|  | 24 h | 88.7% ± 2.0% | 91.8% ± 0.1% | 0.30 |

Hypoxia Increases the Levels of PAI-1 mRNA Through a Mechanism that Involves a Heme Protein The effect of hypoxia on the expression of PAI-1 by human first trimester trophoblast cells (HTR-8/SVneo) was demonstrated at the mRNA level by Northern blot analysis. Progressive time-dependent increases in PAI-1 mRNA (both the 3.0- and 2.3 kb PAI-1 transcripts) were observed in cells cultured under 1% O$_2$ This hypoxia-mediated stimulation of PAI-1 transcripts was evident as early as 2 hours, was elevated about 6-fold from 4 to 12 hours, and about 16- and 32-fold (for the 3.0- and 2.3-kb transcript species respectively) at the 24 hour point.

To assess the possible involvement of a heme protein in the regulation of PAI-1 expression by hypoxia, HTR-8/SVneo cells were cultured for 24 hours in the presence of chemicals such as cobalt chloride and Tiron, which prevent binding of molecular oxygen to heme proteins and thus mimic hypoxia, as well as under hypoxia in the presence or absence of 20% carbon monoxide. Culture under 1% oxygen or in the presence of the iron chelator, Tiron, resulted in a substantial increase in the levels of both the 3.0-kb and the 2.3-kb and the 2.3-kb PAI-1 transcripts. Similarly, culture in the presence of cobalt chloride produced an increase of about 2-fold, whereas inclusion of 20% carbon monoxide in the hypoxic environment prevented most of the hypoxia-mediated increase in PAI-1 mRNA levels. These finding demonstrate that hypoxia up-regulates PAI-1 expression at the mRNA level in first trimester invasive trophoblast cells and that this effect is mediated through a heme protein-dependent mechanism.

Hypoxia Increase the Levels of PAI-1 in Culture Medium

ELISA measurements performed in duplicate demonstrated a consistent increase in plasminogen activator inhibitor-1 levels in the condition medium of HTR-8/SVneo cells cultured under 1% oxygen, beginning at 4 hours and continuing at 8, 12 and 24 hours, compared with 20% oxygen (Table 2). Although no stimulation in PAI-1 protein secretion was observed at less than 2 hours of hypoxic exposure, the PAI-1 levels were nearly two-fold higher in the hypoxia versus the normoxia group as early as the 8 hour time point.

TABLE 2

Measurement of PAI-1 levels in the culture medium of HTR-8/SVneo cells by ELISA

|  |  | 20% Oxygen (ng/ml) | 1% Oxygen (ng/ml) | Percent Change |
| --- | --- | --- | --- | --- |
| Experiment 1 | 24 h | 2.054 | 3.414 | 66 |
| Experiment 2 | 24 h | 8.995 | 9.233 | 3 |
| Experiment 3 | 24 h | 5.580 | 12.384 | 122 |
|  | 12 h | 5.725 | 9.745 | 70 |
|  | 8 h | 3.567 | 6.107 | 70 |
| Experiment 4 | 12 h | 5.567 | 8.192 | 47 |
|  | 8 h | 7.721 | 11.131 | 44 |
|  | 4 h | 12.851 | 13.106 | 2 |
| Experiment 5 | 8 h | 2.299 | 4.760 | 107 |
|  | 2 h | 1.218 | 0.266 | 78 |
|  | 1 h | 0.437 | Undetectable |  |
|  | 30 min | Undetectable | Undetectable |  |

Adhesion of HTR-8/SVneo Cells to the ECM Protein Vitronectin is Markedly Reduced By Hypoxia Since PAI-1 has been shown to modulate cell adhesion through its interaction with the ECM protein vitronectin, the effect of hypoxia on the adhesive properties of the human trophoblast cell line HTR-8/SVneo was examined. Adhesion of these cells to vitronectin-coated wells was reduced by approximately 60% when the adhesion assay was conducted under a hypoxic environment with cells that had been previously maintained under hypoxia for 24 hours. Interestingly, the cells' adhesiveness was restored to about 80% of standard levels following re-exposure of the cells to 20% oxygen for a duration of 30 minutes and throughout the adhesion period (45 minutes).

These studies indicate that culture under low levels of oxygen results in up-regulation of PAI-1 expression at the protein and mRNA levels in first trimester invasive trophoblast cells and that this effect is mediated through a heme protein-dependent mechanism. This conclusion is based on observations in which chemicals that prevent binding of oxygen to heme proteins, such as cobalt chloride and Tiron, were able to mimic hypoxia and by the fact that inclusion of carbon monoxide in the hypoxic atmosphere abolished the effect of hypoxia on PAI-1 mRNA levels.

EXAMPLE 3

Identification of RTP/Drg1 Gene Induced By Hypoxia By mRNA Differential Display

The mRNA differential display technique (Liang, P. and Pardee, A. B. Science 257:967–971 (1992)) was used to compare gene expression in cells cultured under 1% oxygen or 20% oxygen. Each experiment was performed in triplicate to assure reproducibility. A representative autoradiogram obtained by differential display analysis of MDA-MB-231 cells cultured under 20% oxygen and 1% oxygen is shown in FIG. 1. cDNA bands exhibiting differential intensities were excised from the gels, cloned, and used as probes for Northern blotting.

One particular clone appeared to be markedly up-regulated in all gels examined. Upon sequence analysis, the isolated 312-bp cDNA fragment displayed 100% similarity to a gene previously identified by three separate groups, termed RTP (reducing agents and tunicamycin-responsive protein) (Kokame, K., et al., J Biol Chem 271:29659–29665 (1996)), Drg1 (differentiation-related gene 1) (van Belzen, N., et al., Lab Invest 77:85–92 (1997)), and Cap43 (Zhou, D., et al., Cancer Res 58:2182–2189 (1998)). Furthermore, the full cDNA sequence of the gene has been resolved and found to consist of 3056 bp (Kokame, K., et al., J Biol Chem 271:29659–29665 (1996)). Effect of Exposure to Hypoxia on RTP/Drg1 mRNA Levels.

Figure 2A:
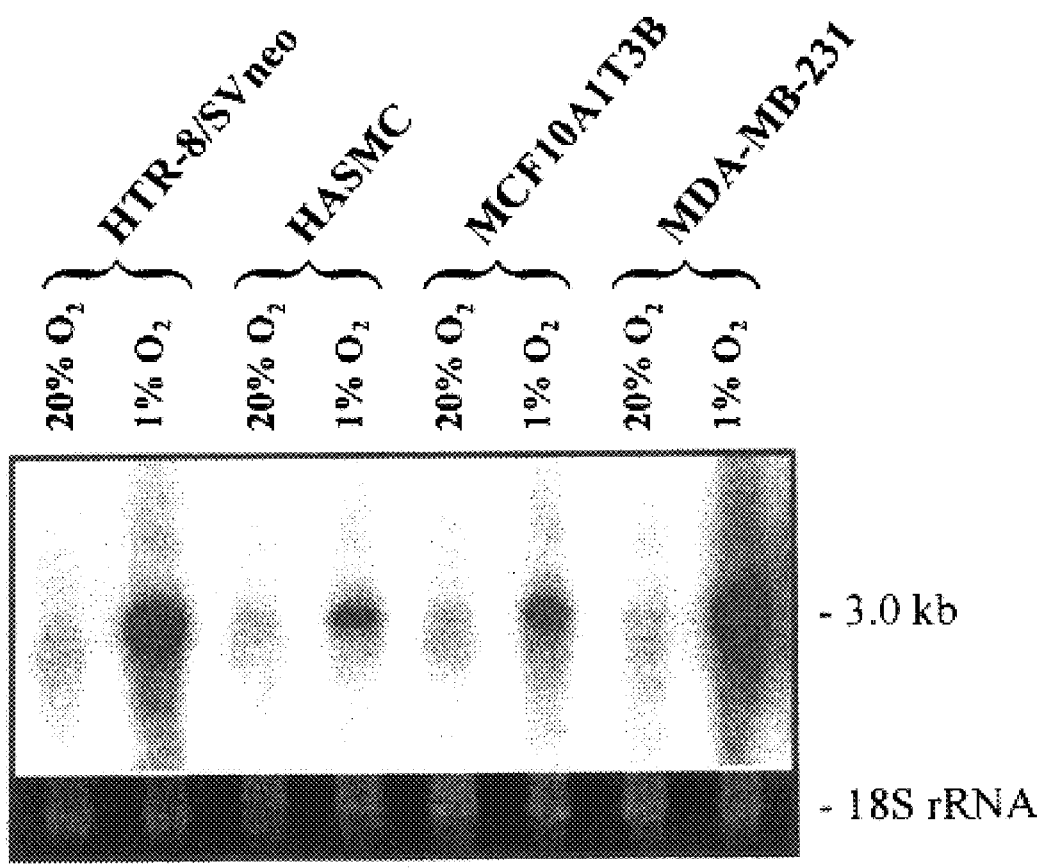
FIG. 2A is a Northern blot showing that culture of HTR-8/SVneo first trimester trophoblasts, human aortic smooth muscle cells (HASMC), as well as MCF10A1T3B and MDA-MB-231 breast carcinoma cells for 24 h under 1% oxygen resulted in marked increases in the 3-kb RTP/Drg1 transcript levels, compared with culture under standard conditions (20% oxygen). Ethidium bromide staining of 18S rRNA was used to indicate the relative amount of RNA loaded in each lane. The experiments shown in this figure were repeated at least twice and similar results were obtained each time.
Figure 2B:
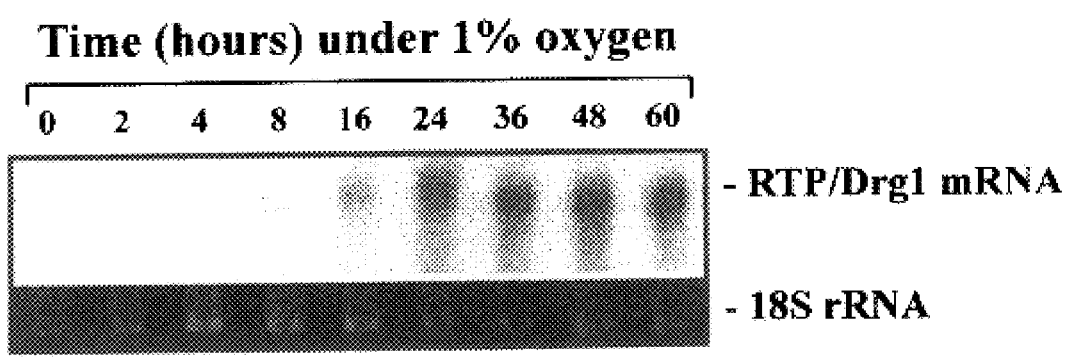
FIG. 2B is a Northern blot showing the time-course of hypoxia induced RTP/Drg1 transcript expression in MDA-MB-231 cells. Maximal mRNA levels were reached at 24 h of hypoxic culture and they remained high thereafter. Ethidium bromide staining of 18S rRNA was used to indicate the relative amount of RNA loaded in each lane. The experiments shown in this figure were repeated at least twice and similar results were obtained each time.
Figure 2C:
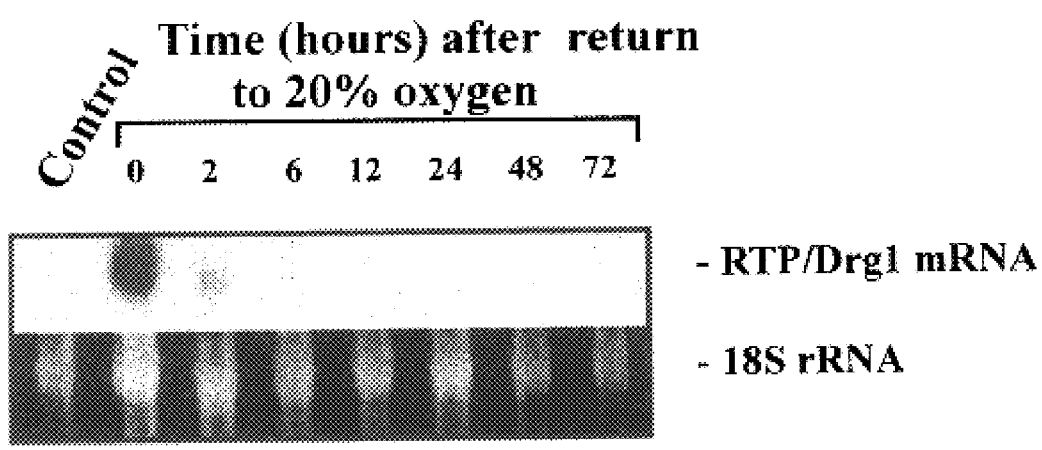
FIG. 2C is a Northern blot showing that reoxygination suppressed expression of RTP/Drg1 transcripts. After a 24-h incubation under 1% oxygen, cultures of MDA-MB-231 cells were placed in a standard incubator at 20% oxygen to determine the effect of reoxygenation on RTP/Drg1 mRNA levels. Transcript levels were markedly reduced after 2 h of re-exposure to higher $pO_2$ values and returned to near-control amounts by 6 h. Ethidium bromide staining of 18S rRNA was used to indicate the relative amount of RNA loaded in each lane. The experiments shown in this figure were repeated at least twice and similar results were obtained each time.
Figure 2D:
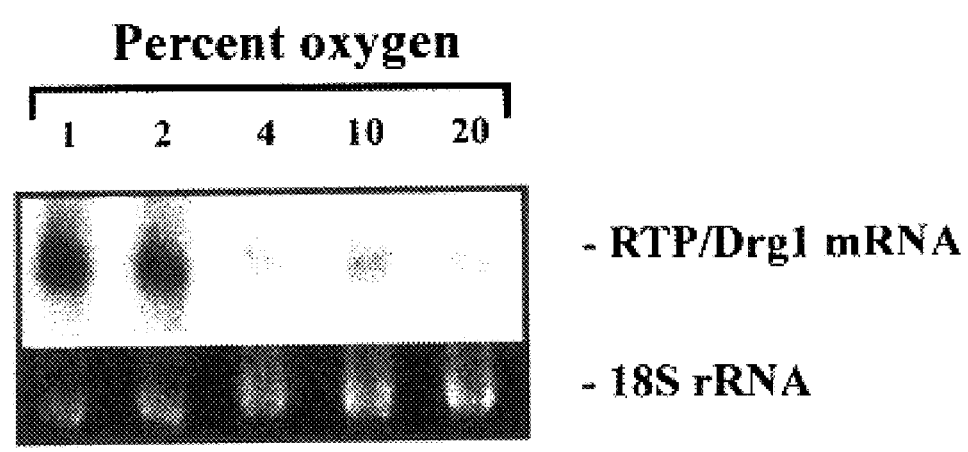
FIG. 2D is a Northern blot showing marked increases in RTP/Drg1 mRNA levels in MDA-MB-231 cells cultured under 1% and 2% oxygen but not in cells cultured under 4%, 10%, or 20% oxygen. Ethidium bromide staining of 18S rRNA was used to indicate the relative amount of RNA loaded in each lane. The experiments shown in this figure were repeated at least twice and similar results were obtained each time. The data in this figure are representative of two or more independent experiments showing similar results.

Northern blot analysis revealed that, following hypoxic culture, the levels of RTP/Drg1 mRNA were substantially increased (over 16-fold) in the HTR-8/SVneo trophoblast cells, the MDA-MB-231 and MCF 10A1T3B breast carcinoma cells, and in the human aortic smooth muscle cells (FIG. 2A). The induction of RTP/Drg1 mRNA in MDA-MB-231 cells was first apparent after 8 h of exposure to hypoxia, reached a maximum at 24 h, and remained high for at least 60 h (FIG. 2B). Viability of the MDA-MB-231 cells incubated under 1% oxygen, as assessed by trypan blue exclusion and LDH accumulation, also remained high for at least 48 h (data not shown). Following a 24-h incubation of MDA-MB-231 cells under 1% oxygen, a 2-h re-exposure to standard (20% oxygen) conditions was sufficient to substantially reduce RTP/Drg1 mRNA levels (FIG. 2C). Oxygen dose-dependent response analysis revealed markedly increased RTP/Drg1 mRNA levels in cells cultured under 1% or 2% oxygen for 24 h (16- and 10-fold respectively; FIG. 2D). In contrast, compared with culture under 20% oxygen, culture under 4% oxygen did not result in increased RTP/Drg1 transcript levels (FIG. 2D). Expression of RTP/Drg1 Protein.

Figure 3A:
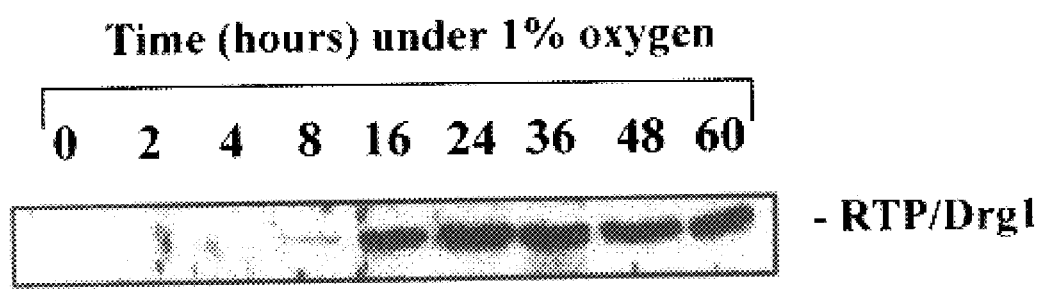
FIG. 3A is a Western blot showing that MDA-MB-23 cells displayed peak levels of the 43-kDa protein when cultured under hypoxia for 16–24 h, and that the level of 43-kDa protein remained high thereafter. The data in this figure are representative of two or more independent experiments showing similar results.
Figure 3B:
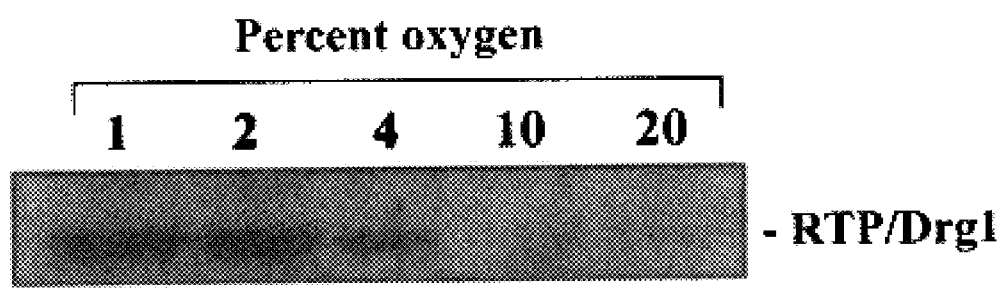
FIG. 3B is a Western blot showing that culture of MDA-MB-23 cells under 4% oxygen resulted in increased expression of the 43-kDa protein, the highest levels of the 43-kDa protein were observed in cells cultured under either 2% or 1% oxygen, in a manner similar to that observed for RTP/Drg1 mRNA levels (FIG. 2D). The data in this figure are representative of two or more independent experiments showing similar results.
Figure 3C:
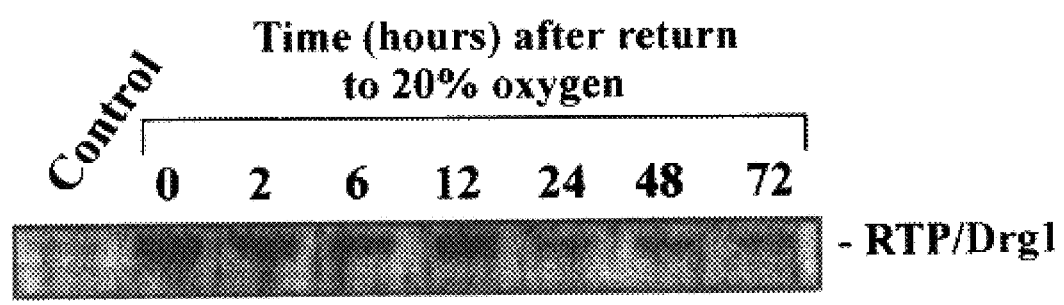
FIG. 3C is a Western blot showing that RTP/Drg1 protein levels in MDA-M-23 cells remained high even 48 h after return of the cultures to 20% oxygen. The data in this figure are representative of two or more independent experiments showing similar results.

The anti-Drg1 antiserum recognized a protein of the expected 43-kDa size in Western blots. Increase in RTP/Drg1 protein was first apparent in MDA-MB-231 cells following 8 h culture under 1% oxygen (FIG. 3A). However, the highest levels of the 43-kDa protein were observed in cells cultured under 1% oxygen for at least 24 h (FIG. 3A). Although incubation for 24 h under 4% oxygen resulted in increased levels of protein, the highest levels were observed in cells cultured under 1% or 2% oxygen (FIG. 3B). In contrast to RTP/Drg1 mRNA levels, which reversed to control values soon after re-exposure to higher oxygen levels, reoxygenation did not result in any substantial drop in the levels of the 43-kDa protein for at least 12 h (FIG. 3C).

To further investigate the role of hypoxia on the expression of RTP/Drg1 protein, three-dimensional aggregates of HTR-8/SVneo trophoblast and MDA-MB-231 breast carcinoma cells as models of tissue hypoxia were used. It is recognized that oxygen gradients exist between superficial and deeper layers of multicellular spheroids, with the innermost layers being more hypoxic (Waleh, N. S., et al., *Cancer Res* 55:6222–6226 (1995); Sutherland, R. M., et al., *Cancer Res* 46:5320–5329 (1986)). Spheroids cultured under standard (20% oxygen) conditions exhibited nuclear and cytoplasmic RTP/Drg1 protein immunolocalization in cells within the deeper hypoxic layers, while cells in the more superficial layers remained unlabeled. In contrast, RTP/Drg1 staining was observed throughout entire aggregates, including the cells in the superficial layers, when spheroids were incubated for 24 h under 1% oxygen. Similar staining patterns were observed in MDA-MB-231 spheroids cultured under 20% and 1% oxygen (data not shown).

Role of a Heme Protein in the Hypoxic Regulation of RTP/Drg1 Expression

Figure 4A:
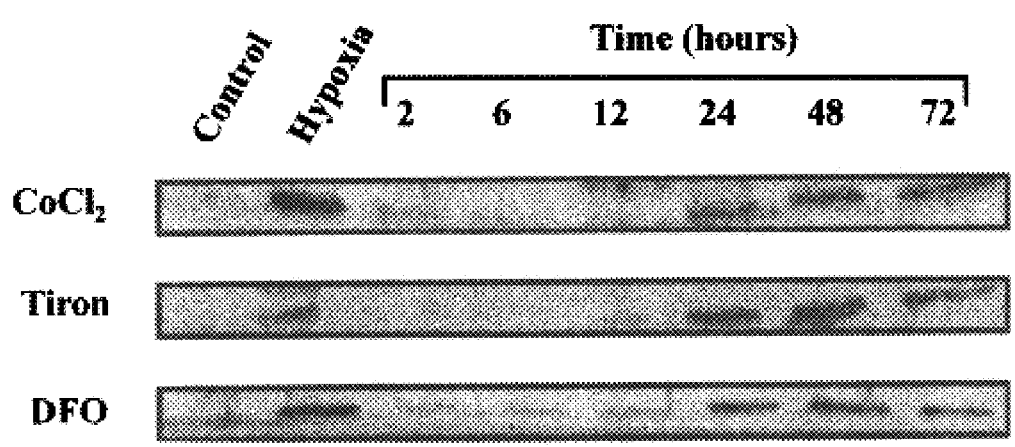
FIG. 4A is a Western blot showing the effect of cobalt chloride, Tiron, and desferrioxamine mesylate (DFO) on the levels of RTP/Drg1 protein in MDA-MB-231 cells. Culture for up to 72 h, under 20% oxygen, in the presence of these compounds resulted in time-dependent increases in RTP/Drg1 protein. In a manner similar to hypoxic cultures, peak protein levels were observed after 24 h of culture. The data in this figure are representative of three independent experiments exhibiting similar results.
Figure 4B:
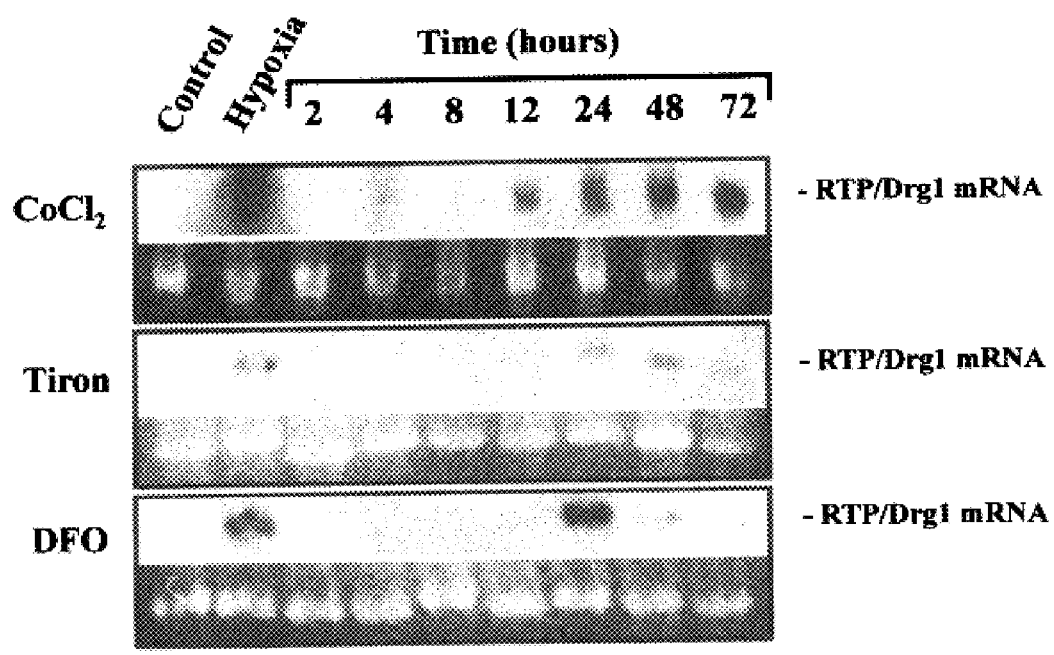
FIG. 4B is a Northern blot showing the effect of cobalt chloride, Tiron, and desferrioxamine mesylate (DFO) on the levels of RTP/Drg1 mRNA in MDA-MB-231 cells. Culture for up to 72 h, under 20% oxygen, in the presence of these compounds resulted in time-dependent increases in RTP/Drg1 mRNA. In a manner similar to hypoxic cultures, peak mRNA levels were observed after 24 h of culture. The data in this figure are representative of three independent experiments exhibiting similar results.
Figure 5A:
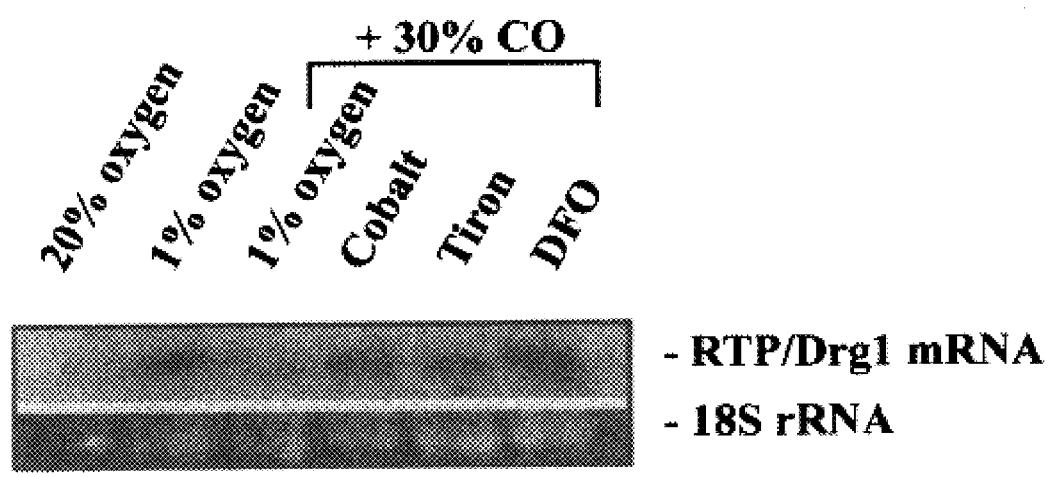
FIG. 5A is a Northern Blot showing the effect of carbon monoxide (CO) on the hypoxic up-regulation of RTP/Drg1 expression. In contrast to cultures incubated under standard conditions (20% oxygen), culture of MDA-MB-231 cells under 1% oxygen for 24 h resulted in increased RTP/Drg1 mRNA. This up-regulation was inhibited in parallel cultures by inclusion of 30% CO in the hypoxic atmosphere, which resulted in a substantial decrease in mRNA levels (third lane). In contrast, CO was unable to inhibit the up-regulation of RTP/Drg1 expression induced by cobalt chloride, Tiron and DFO (lanes 4–6).
Figure 5B:
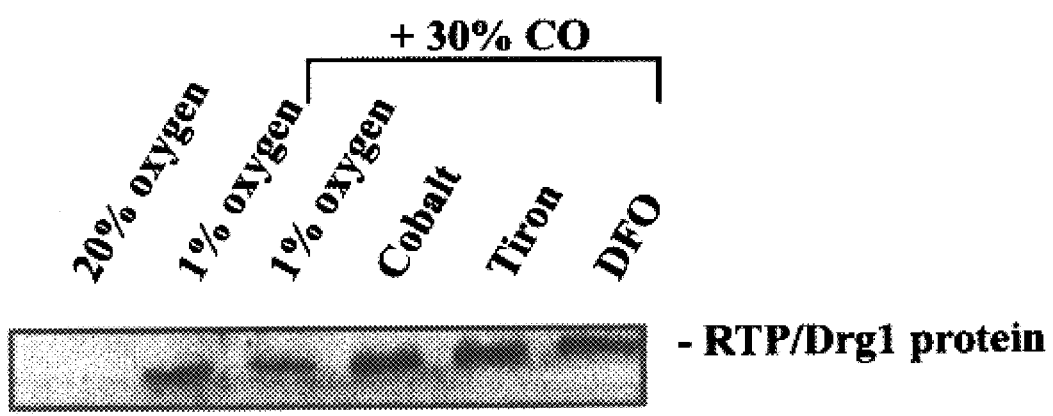
FIG. 5B is a Western Blot showing the effect of carbon monoxide (CO) on the hypoxic up-regulation of RTP/Drg1 expression. In contrast to cultures incubated under standard conditions (20% oxygen), culture of MDA-MB-231 cells under 1% oxygen for 24 h resulted in increased RTP/Drg1 protein levels. This up-regulation was inhibited in parallel cultures by inclusion of 30% CO in the hypoxic atmosphere, which resulted in a 57% reduction in protein levels (third lane), as determined by densitometry. In contrast, CO was unable to inhibit the up-regulation of RTP/Drg1 expression induced by cobalt chloride, Tiron and DFO (lanes 4–6).

If certain hypoxic responses are mediated through a putative iron-containing heme protein, the deoxy conformation of such protein can be maintained by replacing the iron atom within the porphyrin ring of the heme moiety with metals that do not bind oxygen or do so with very low affinity, such as cobalt, or by chelating iron with compounds such as Tiron or desferrioxamine (DFO). Culture of MDA-MB-231 cells for up to 72 h, under 20% oxygen, with 100 $\mu$M cobalt chloride, 30 MM Tiron, or 100 $\mu$M DFO resulted in time-dependent increases in RTP/Drg1 protein (FIG. 4A) and mRNA (FIG. 4B). Furthermore, presence of 30% carbon monoxide in the hypoxic atmosphere abrogated the hypoxic up-regulation of RTP/Drg1 mRNA (FIG. 5A) and protein (FIG. 5B). Like oxygen, carbon monoxide binds to heme proteins and maintains them in the oxy conformation, thereby blocking heme protein-mediated hypoxic responses. To rule out the possibility that the inhibition of the hypoxic effect by carbon monoxide was not due to non-specific toxicity on the cells, we cultured MDA-MB-231 cells with cobalt chloride, Tiron and DFO under hypoxic conditions in the presence of carbon monoxide. Western and Northern blot analysis revealed that the presence of carbon monoxide in the atmosphere did not inhibit the up-regulation of RTP/Drg1 expression induced by cobalt chloride, Tiron and DFO (FIGS. 5A and 5B). RTP/DRG1 message is elevated in preeclamptic placental tissues.

Figure 6:
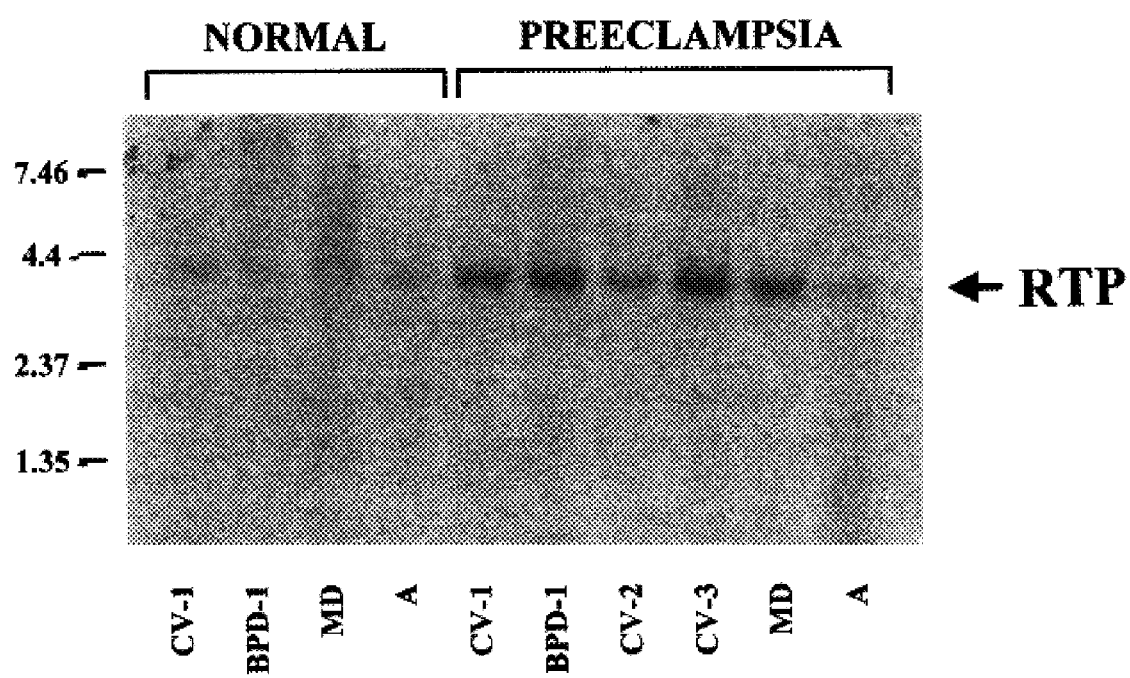
FIG. 6 is a northern blot showing that RTP/Drg1 message is expressed at higher levels in tissues isolated from preeclamptic pregnancies than in tissues isolated from normal pregnancies. CV=chorionic villi, BPD=basal plate decidua, MD=membrane decidua, A=amnion (amniotic membrane).

RTP/Drg1 message levels were measured in placental tissues from normal pregnancy and preeclampsia by northern blot analysis (FIG. 6). Levels of message are indicated by the intensity of the bands. CV=chorionic villi, BPD= basal plate decidua, MD=membrane decidua, A=amnion (amniotic membrane). Note higher intensity in the RTP-Drg1 bands in tissues isolated from preeclamptic pregnancies. Expression pattern of RTP/Drg1 (PROXY-1) message in placental tissue.

The expression pattern of RTP/Drg1 (PROXY-1) message was analyzed by in situ hybridization analysis of placental tissue sections. Antisense or sense (negative control) radiolabelled RTP/Drg1 cRNA probes (riboprobes) were incubated with placental chorionic villi or placental membranes (decidua and chorion) isolated from women with either normal pregnancies or preeclampsia at full term of gestation. Hybridization reactions were detected by the presence of grains in the photographic emulsion (white dots in dark-field images). A higher number of hybridization grains were detected in tissues isolated from preeclamptic pregnancies as compared with normal tissues. Hybridization grains were observed overlying all cell types present in the tissues, indicating that all of the cell types in these tissues are capable of expressing RTP/Drg1 message. Relatively few hybridization grains were detected in sections incubated with sense probe (negative controls: should not hybridize with RTP/Drg1 message) and indicate background. These results suggest that placental tissues from preeclamptic pregnancies are exposed to lower levels of oxygen than similar tissues isolated from normal pregnancies (FIGS. 25A–25D, and data not shown).

EXAMPLE 4

Urokinase Receptor Expression is Stimulated by Hypoxia

Figure 7:
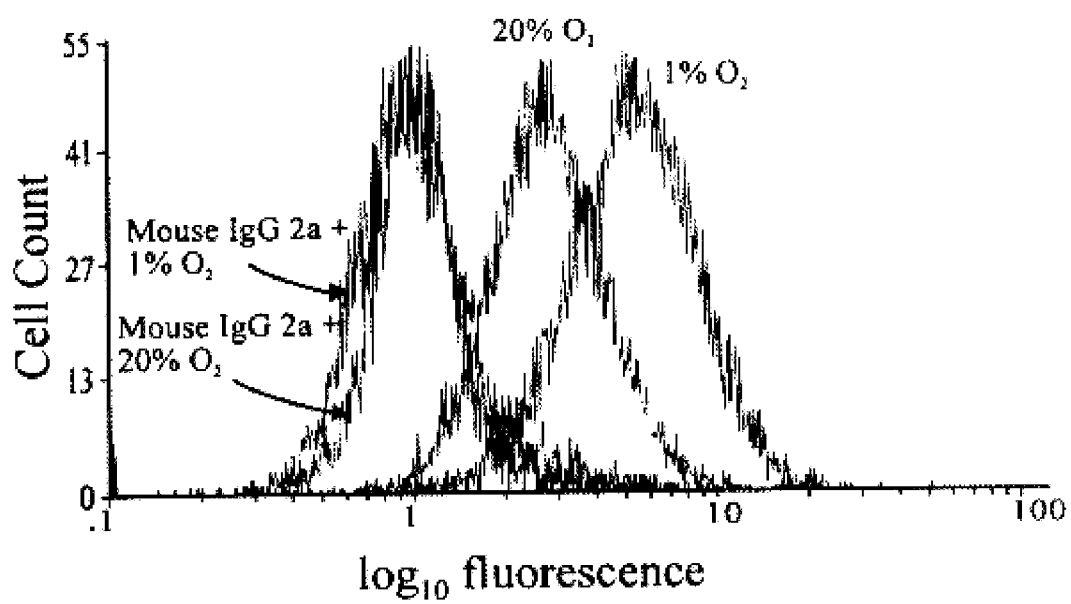
FIG. 7 is a histogram showing augmented expression of uPAR on cells cultured under hypoxic conditions. Analysis of uPAR expression by HTR-8/SVneo cells using flow cytometry revealed an average increase of 68% in the mean fluorescence intensity when cells were cultured under hypoxic conditions and labeled with mAb 3937. This figure is representative of 7 independent experiments.
Figure 8:
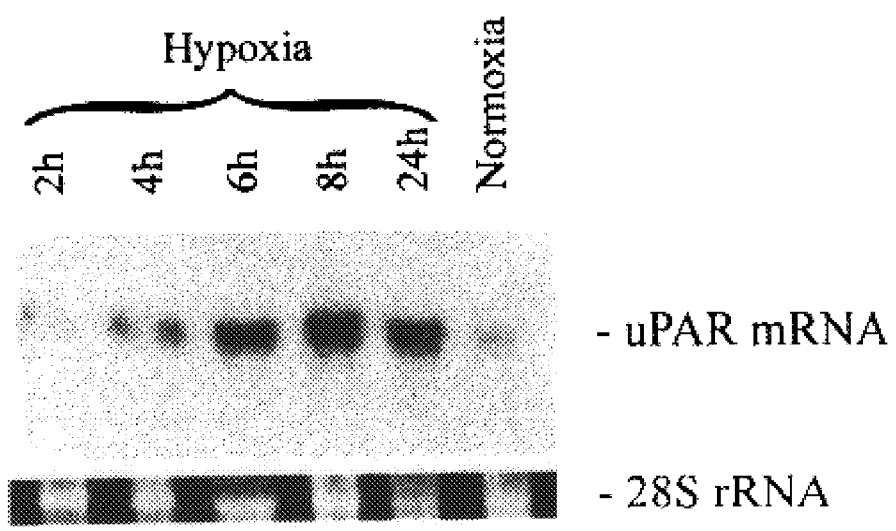
FIG. 8 is a Northern blot showing increased expression of uPAR mRNA in cells cultured under hypoxic conditions. uPAR mRNA levels increased 2.5-fold after only 4 h of hypoxic culture compared with uPAR mRNA levels in cells cultured under standard conditions. The levels of uPAR transcript increased 5-fold at 6 h of culture under hypoxia and remained high at 8 and 24 h. Relative levels of uPAR mRNA were determined with a SigmaGel gel analysis program using 28S rRNA to correct for differences in the amount of RNA loaded onto the gel.

The effect of hypoxia on the expression of uPAR by HTR-8/Svneo cells (FIG. 7) was determined. In comparison to cells cultured under standard conditions (20% $O_2$), the expression of uPAR by cells cultured in 1% $O_2$ for 24 h was 68% higher (n=7, P=0.007), as determined by flow cytometry. Equal amounts of non-immune mouse $IgG_{2a}$ bound to cells cultured under both standard and hypoxic conditions, demonstrating that increased binding of anti-uPAR mAb 3937 was not due to non-specific interactions, or increased Fc$\gamma$ receptor expression. Similarly, assessment of uPAR expression by HTR-8/SVneo cells through measurement of [$^{125}$I]-prourokinase binding revealed that hypoxia stimulated the expression of uPAR by 88% (n=9, P=0.003), an increment similar to that detected using flow cytometry. This was accompanied by a parallel increase in the $K_d$ (Table 3), as well as by an increase in the cellular content of uPAR mRNA (FIG. 8). Increased uPAR mRNA expression was first apparent after 4 h of exposure to hypoxia, and reached a maximum level after 6 h.

Figure 9:
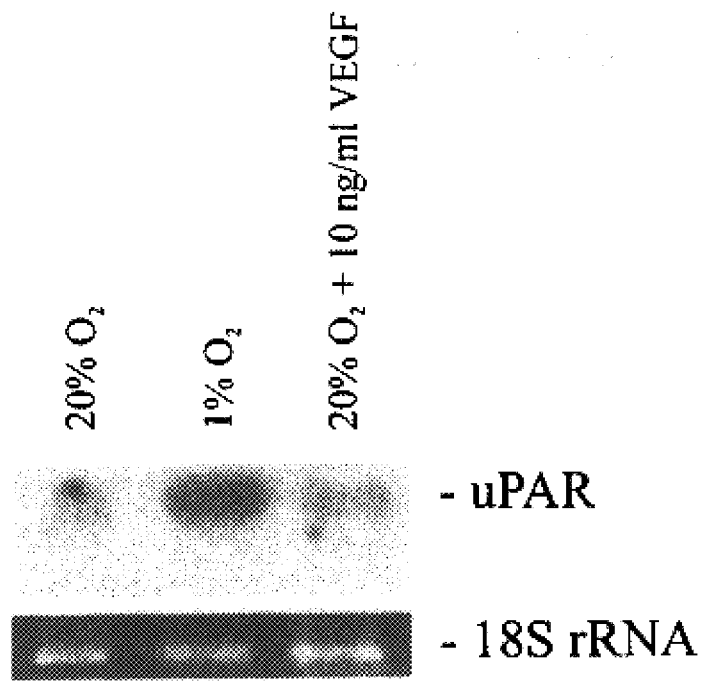
FIG. 9 is a Northern blot showing that vascular endothelial cell growth factor (VEGF) does not induce uPAR mRNA in HTR-8/SVneo cells cultured under normoxic conditions.

It has been reported that VEGF increases the expression of uPAR by vascular endothelial cells (Mandriota S J, et al., *J Biol Chem* 270:9709 (1995)). Furthermore, recent studies have shown that hypoxia stimulates VEGF release by increasing transcriptional activation of the VEGF gene via hypoxia-inducible factor-1 (HIF-1 ) as well as through mRNA stabilization (Shweiki D, et al., *Proc Natl Acad Sci USA* 92:768 (1995), Minchenko A, et al. *Lab Invest* 71:374 (1994), Forsythe J A, et al., *Mol Cell Biol* 16:4604 (1996), White F C, et al. *Growth Factors* 12:289 (1995). In the present study, however, culture of HTR-8/SVneo cells in the presence of 10 ng/ml of VEGF for 24 h under normoxic conditions did not result in increased levels of uPAR transcript above control values (FIG. 9), suggesting that the hypoxia-mediated upregulation of uPAR occurs through a VEGF-independent mechanism.

Figure 10:
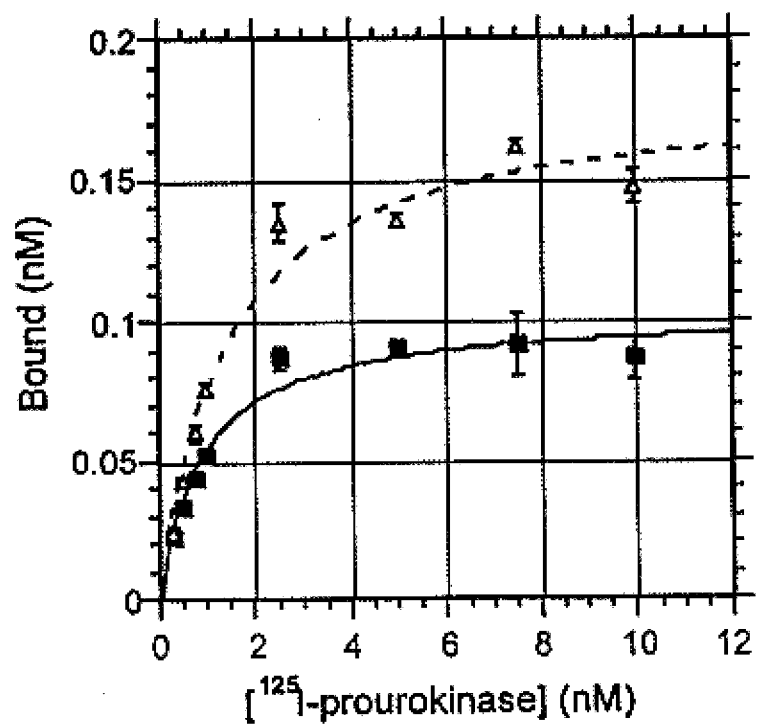
FIG. 10 is a graph showing dose dependant binding of $^{125}$I-prourokinase to human umbilical vein endothelial cells (HUVEC) under standard (solid squares) and hypoxic (open triangles) conditions. This figure is representative of three independent experiments, in which a mean increase of 46% in the binding of [$^{125}$I]-prourokinase to cells cultured under hypoxic conditions was observed. Error bars indicate standard error of triplicate samples for each point.

Whether the effects of hypoxia on uPAR expression extended to other cell types such as endothelial cells was investigated. FIG. 10 shows results in which similar effects of hypoxia on up-regulation of uPAR expression were detected by radioligand binding studies using human umbilical vein endothelial cells. These results were also confirmed by flow cytometry (not shown).

TABLE 3

Effects of hypoxia, Tiron and cobalt chloride on the binding of [$^{125}$I]-prourokinase to HTR-8/SVneo cells

| Condition | $B_{max}$ (sites/cell) ± SEM | $K_d$ (nM) ± SEM | P ($B_{max}$) | P ($K_d$) | n |
|---|---|---|---|---|---|
| Standard vs. Hypoxia: | | | | | |
| Standard | 189,028 ± 39,222 | 1.26 ± 0.16 | | | 9 |
| Hypoxia | 356,728 ± 64,488 | 2.18 ± 0.42 | 0.003 | 0.025 | 9 |
| Standard vs. Tiron: | | | | | |
| Standard | 208,980 ± 26,825 | 2.93 ± 0.59 | | | 6 |
| Tiron | 623,213 ± 102,360 | 8.08 ± 1.11 | 0.004 | 0.001 | 6 |

TABLE 3-continued

Effects of hypoxia, Tiron and cobalt chloride on the binding of [$^{125}$I]-prourokinase to HTR-8/SVneo cells

| Condition | $B_{max}$ (sites/cell) ± SEM | $K_d$ (nM) ± SEM | P ($B_{max}$) | P ($K_d$) | n |
|---|---|---|---|---|---|
| Standard vs. Cobalt Chloride: | | | | | |
| Standard | 223,026 ± 37,035 | 2.49 ± 0.47 | | | 8 |
| Cobalt Chloride | 285,711 ± 38,324 | 3.58 ± 0.69 | 0.014 | 0.004 | 8 |

Role of a Heme Protein in the Regulation of uPAR Expression

Figure 11:
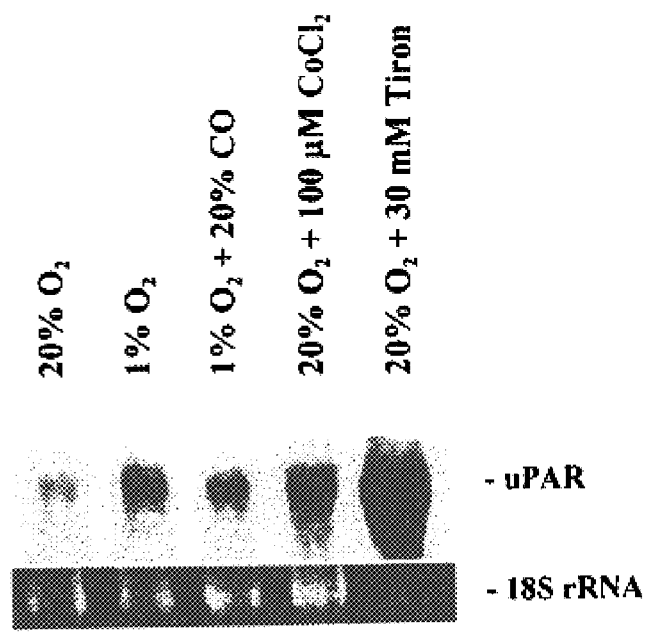
FIG. 11 is a Northern blot showing the effect of hypoxia, carbon monoxide, cobalt chloride and Tiron on the levels of uPAR mRNA in HTR-8/SVneo cells. Cells were cultured for 24 h under the conditions listed under each lane of the figure. Levels of uPAR mRNA were increased 2.8, 1.8, 3.5 and >10-fold, respectively, within cells cultured under hypoxic (1% $O_2$) conditions, hypoxic conditions in the presence of 20% carbon monoxide, and standard (20% $O_2$) conditions in the presence of either cobalt chloride or Tiron, in comparison to cells cultured under standard conditions alone (lane 1). Carbon monoxide reduced the hypoxia-mediated increase in uPAR mRNA by 35%.

To examine the potential involvement of a heme protein in the hypoxia-mediated stimulation of uPAR expression, the expression of uPAR by HTR-8/SVneo cells in response to incubation in the presence of cobalt chloride or Tiron was examined. Both flow cytometric and radioligand binding studies revealed a 3-fold increase in the expression of uPAR in response to Tiron (n=6, P=0.004), with a more modest 28% increase observed in response to cobalt chloride (n=8, P=0.014; Table 3). In each case, the $K_d$ increased as well, as observed following exposure of cells to hypoxia. Stimulation of uPAR expression by either cobalt or Tiron was associated with increased levels of uPAR mRNA, comparable to those observed in response to hypoxia (FIG. 11).

Figure 12:
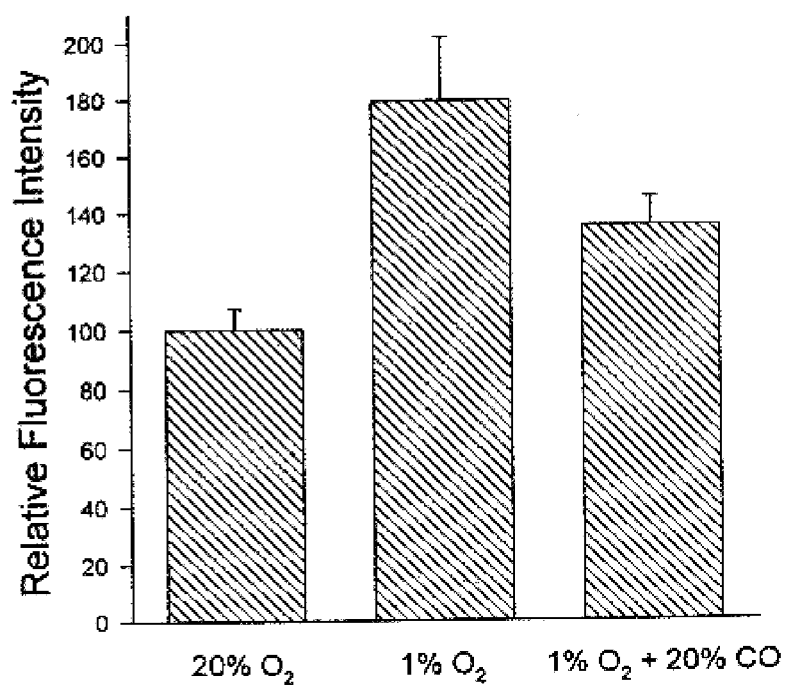
FIG. 12 is a graph showing inhibition of hypoxia-induced uPAR expression by carbon monoxide. HTR-8/SVneo cells were incubated for 24 h under standard (20% $O_2$) or hypoxic (1% $O_2$) conditions, or hypoxic conditions in the presence of 20% carbon monoxide. The expression of uPAR was then assessed by flow cytometry using mAb 3937. Carbon monoxide inhibited the hypoxia-induced expression of uPAR by 56%. Data represent the mean±standard error of 4 independent experiments.

To further assess the potential role of a heme protein in the increased expression of uPAR in response to hypoxia, we assessed the effects of carbon monoxide on this response. As expected, increased uPAR expression following culture of HTR-8/SVneo cells under hypoxic (1% oxygen) conditions was inhibited (56%) by inclusion of 20% carbon monoxide in the gas mixture (FIG. 12); a parallel decrease was observed in the content of cellular uPAR mRNA (FIG. 11). Furthermore, in two independent experiments, the inhibitory effects of carbon monoxide on the hypoxia-induced expression of uPAR were completely prevented by inclusion of cobalt chloride or Tiron in the medium (not shown), demonstrating that the inhibition of uPAR expression by CO under hypoxic conditions was not due to nonspecific toxicity.

Hypoxia Stimulates In vitro Invasiveness Via a Heme Protein

To determine the functional correlates of hypoxia-induced uPAR expression, the invasion of HTR-8/SVneo cells through a reconstituted basement membrane (Matrigel) under standard (20% oxygen) and hypoxic (1% oxygen) conditions were compared. A 41.4%±7.4% (P=0.003) increase in invasion was observed when HTR-8/SVneo cells was were cultured under hypoxic conditions (Table 4). Similar increases were observed when invasion assays were performed under 20% oxygen in the presence of either 100 μM cobalt chloride (24.6±8.4%; P=0.028) or 30 mM Tiron (29.3±12.7%; P=0.035) (Table 4). The role of a heme protein in the regulation of cellular invasiveness was confirmed by experiments in which hypoxia-stimulated invasion was inhibited by 87% in the presence of 20% carbon monoxide, and was not significantly different from that which occurred in the presence of 20% oxygen (Table 4).

TABLE 4

Effects of hypoxia, carbon monoxide, Tiron and cobalt chloride on invasion of HTR-8/SVneo cells through Matrigel

| Condition | Invasion Index* (%) ± SE | P (vs standard) | n |
|---|---|---|---|
| Standard (20% $O_2$) | 100 | | 11 |
| Hypoxia (1% $O_2$) | 141.4 ± 7.4 | 0.003 | 11 |
| Standard + Cobalt Chloride | 124.6 ± 8.4 | 0.028 | 9 |
| Standard + Tiron | 129.3 ± 12.7 | 0.035 | 6 |
| Hypoxia + 20% CO | 104.0 ± 8.5 | 0.684 | 10 |

*The invasion index was calculated as described (Graham CH, et al., Exp Cell Res 206:204 (1993)).

Figure 13:
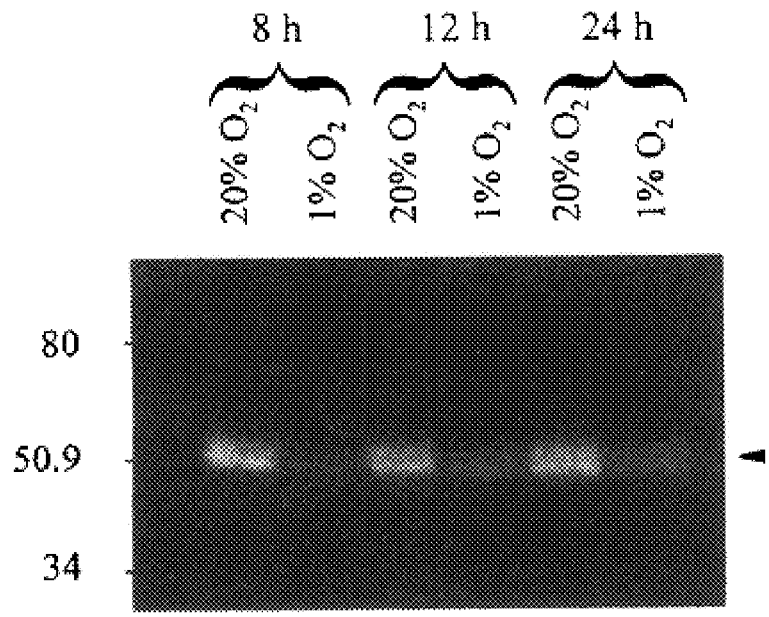
FIG. 13 is a photograph showing zymographic analysis of plasminogen activators present in the medium of HTR-8/SVneo cell cultures incubated for 8, 12 and 24 h under normoxic or hypoxic conditions. Casein and plasminogen were incorporated into the acrylamide prior to polymerization as described (Graham C H, et al., *Exp Cell Res* 206:204 (1993). Samples of serum-free medium containing 200 ng of protein were loaded onto each lane and separated by electrophoresis. Following an overnight incubation in 5 mM $CaCl_2$ in TRIS buffer, gels were stained with Coomassie R-250 in 10% acetic acid/40% methanol and destained in 10% acetic acid/40% methanol. Clear areas represent caseinolytic activity. Note caseinolytic bands at 50–55 kDa corresponding in size to uPA, and that at 24 h of hypoxic culture the caseinolytic bands were not discernible.

Effect of Hypoxia on PA and Gelatinase Levels in Culture Medium, and on Cell Surface Plasminogen Activator Activity Gel zymography revealed a time-dependent reduction in the levels of plasminogen activators in medium conditioned by HTR-8/SVneo cells cultured for up to 24 h under 1% $O_2$ (FIG. 13). These observations were supported by additional studies in which direct measurement of urokinase antigen levels in the conditioned medium of HTR-8/SVneo cells cultured under hypoxic conditions for 24 h were reduced by a mean of 52%. In contrast, the expression of cell surface plasminogen activator activity by HTR-8/SVneo cells cultured for 24 h under hypoxic conditions was 20% higher than that expressed by cells cultured under standard conditions (P=0.000007). These findings are consistent with binding of secreted urokinase to increased numbers of cellular uPAR.

Additional studies in which the levels of gelatinases in the conditioned medium of HTR-8/SVneo cells cultured under standard or hypoxic conditions were assessed by gelatin zymography revealed that hypoxia did not affect the amounts of these proteins released in response to hypoxia (not shown). These observations suggest that the increased invasiveness of HTR-8/Svneo cells observed under hypoxic conditions is not attributable to the increased production or secretion of these proteinases, and instead results from other mechanism, potentially involving increased expression of uPAR.

EXAMPLE 5

Effect of Exposure to Hypoxia on Cell Surface Levels of uPAR

Figure 14:
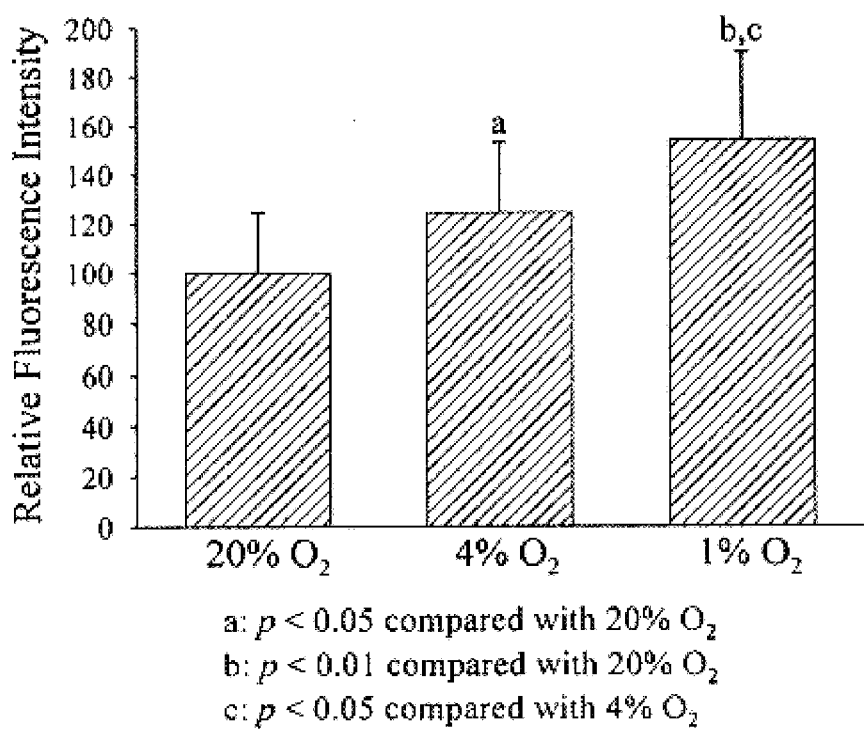
FIG. 14 is a graph illustrating that hypoxia induces the expression of uPAR on MDA-MB-231 cells. Analysis of uPAR expression by cells using flow cytometry revealed an average increase of 54% in the mean fluorescence intensity when cells were cultured under 1% $O_2$ and labeled with mAb 3937 against the human uPAR. Culture under 4% $O_2$ resulted in a more moderate (24%) increase in cell surface uPAR. The latter increase, however, was significantly lower than the increase observed in cells cultured under 1% $O_2$. Bars represent the mean relative fluorescence intensity of 5 independent experiments+S.E. Data were analyzed by a one-way repeated measures ANOVA followed by a post-hoc Newman-Keuls multiple comparisons test for a significant statistic ($p<0.05$).

Compared with culture under standard conditions, culture of MDA-MB-231 cells in 1% $O_2$ for 24 h resulted in a 54% increase in uPAR levels as determined by flow cytometry (FIG. 14). Interestingly, culture under 4% $O_2$ also resulted in increased cell surface uPAR levels as compared with culture under 20% $O_2$. However, these levels were 30% lower than those observed in cells cultured under 1% $O_2$ (FIG. 14). A similar increase (30%, N=3) in uPAR levels was observed in YR-A small cell lung carcinoma cells when cultured under 1% $O_2$ for the same length of time, while a more moderate increase (9%, N=2) was obtained in the MCF-10AT3B cells.

Figure 15:
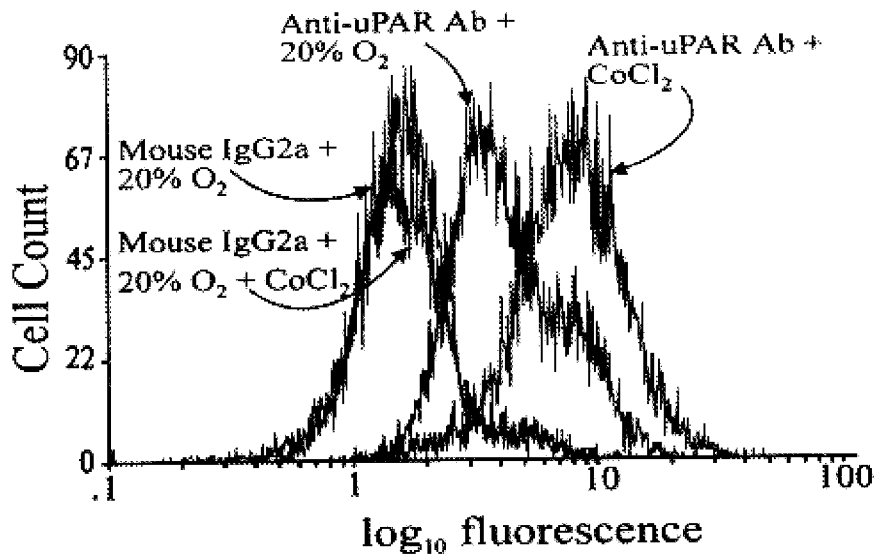
FIG. 15 is a histogram showing that cobalt chloride induces uPAR expression on MDA-MB-231 cells. Analysis of cells cultured under standard conditions in the presence of 100 $\mu$M cobalt chloride revealed a 1.9-fold mean increase in uPAR levels as compared with uPAR levels in cells cultured under standard conditions alone. The data presented were taken from 1 of 2 experiments in which there was a 2.6-fold and 1.2-fold increase, respectively, in relative fluorescence intensity in cells incubated with cobalt chloride.

Whether an iron-containing heme protein is involved in the regulation of cell surface uPAR expression was examined. Therefore, MDA-MB-231 cells were cultured for 24 h in the presence or absence of 100 μM cobalt chloride under standard (20% $O_2$) conditions. Binding of oxygen to the iron atom in the porphyrin ring of heme proteins induces conformational changes from the deoxy, or tense, to the oxy or relaxed state. The deoxy conformation of heme proteins can initiate signaling pathways that lead to increased transcription of hypoxia-regulated genes. In addition to hypoxia, the deoxy (active) conformation can be maintained by substituting the iron molecule within the porphyrin ring with elements like cobalt, that either do not bind oxygen or do so with low affinity, or by culturing cells with iron chelating agents, such as sodium 4,5-dihydroxybenzene-1,3-disulfonate (Tiron) or desferrioxamine. In this study, culture of MDA-MB-231 cells in the presence of cobalt chloride for 24 h resulted in an increase in surface uPAR levels (FIG. 15).

Figure 16:
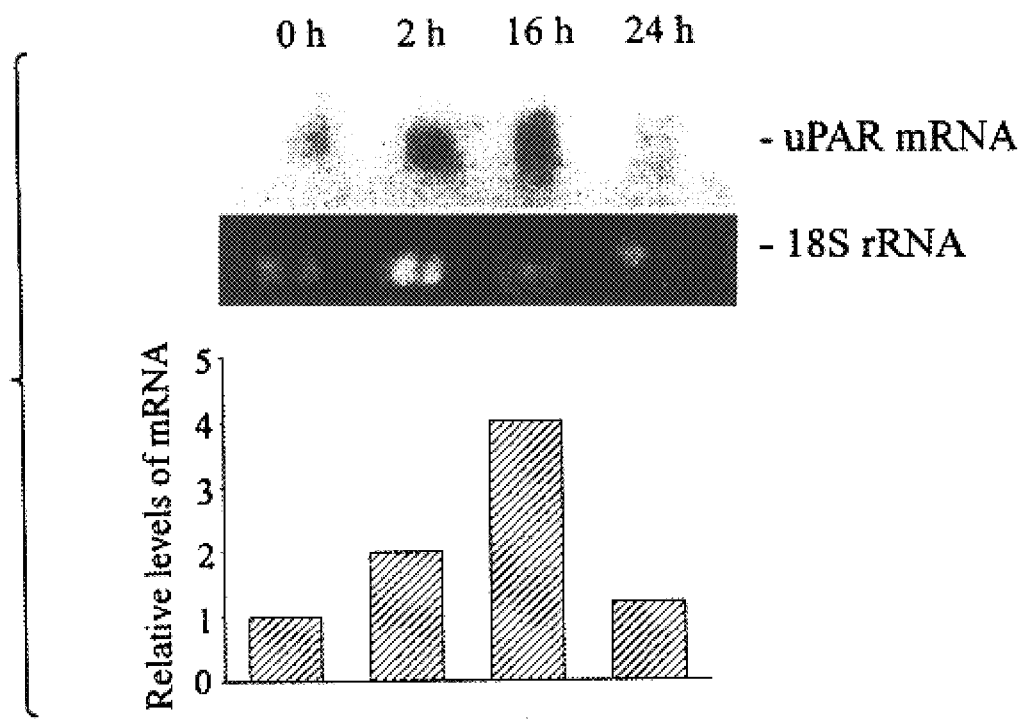
FIG. 16 is a Northern blot and a graph showing the time course for hypoxia-induced increase in uPAR mRNA. Urokinase receptor mRNA levels in MCF-10AT3B breast tumor cells cultured under standard conditions (0 h) or hypoxia (1% $O_2$) for 2, 16 and 24 h as determined by Northern blot analysis. Transcript levels remained high between 2 and 16 h of hypoxic culture and returned to near-control values by 24 h. 18S ribosomal RNA labeled with ethidium bromide was used to correct for differences in the loading of the agarose gel.
Figure 17:
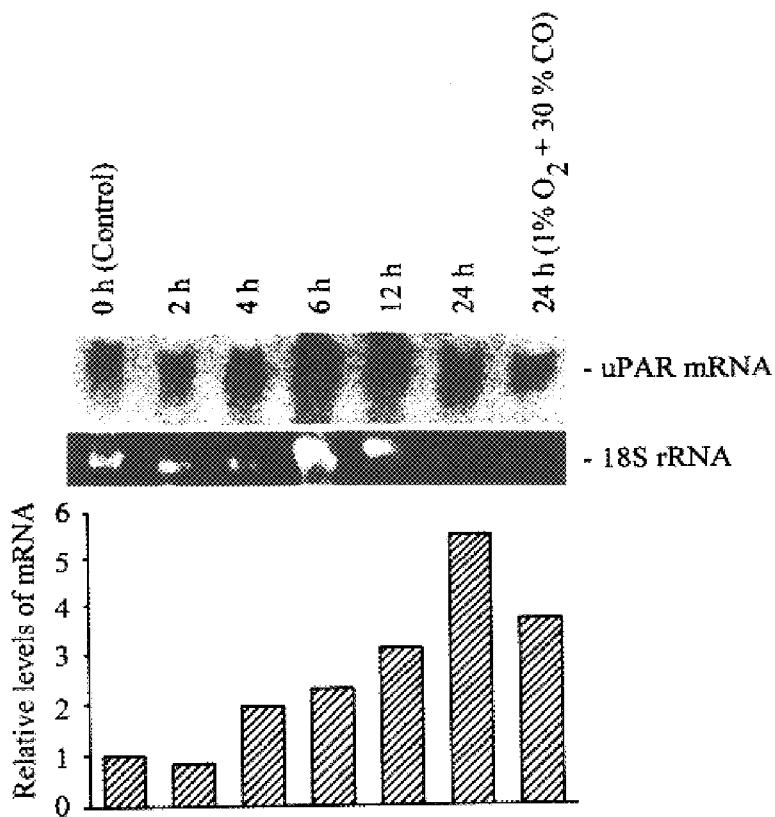
FIG. 17 is a Northern blot and a graph showing the effect of culture for 0, 2, 4, 6, 12 and 24 h under hypoxic conditions, as well as for 24 h under hypoxic conditions in combination with 30% CO, on uPAR mRNA levels in MDA-MB-231 breast carcinoma cells. In these cells, maximum levels of uPAR transcript were observed at 24 h of hypoxic culture. Compared with cells cultured for 24 h under hypoxic conditions alone, culture of cells for a similar length of time with 30% CO in the hypoxic atmosphere resulted in a 33% decrease in the levels of uPAR mRNA.
Figure 18:
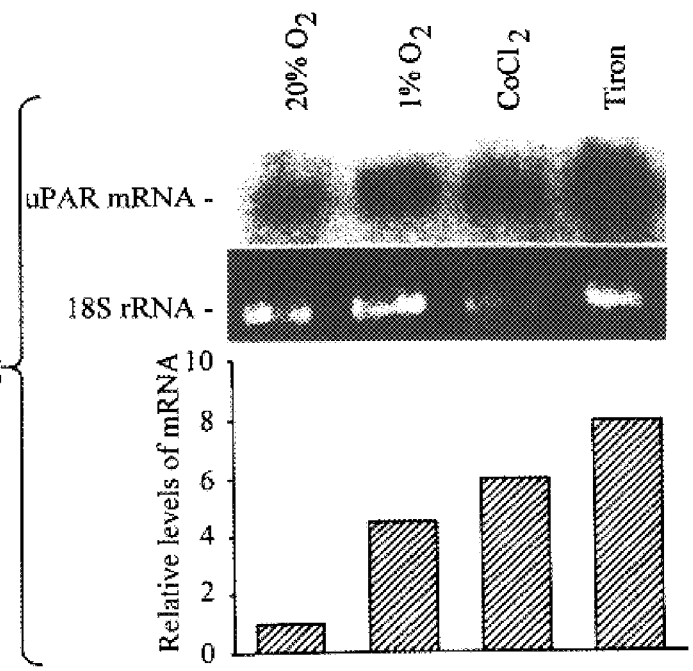
FIG. 18 is a Northern blot and a graph showing the effect of hypoxia, cobalt chloride ($CoCl_2$) and Tiron on uPAR mRNA levels in MDA-MB-231 cells. Densitometric analysis revealed a 4.5-fold increase in uPAR mRNA levels in cells cultured under hypoxia (1% $O_2$) as compared to uPAR levels in cells cultured under standard conditions. Similarly, culture under standard conditions in the presence of 100 $\mu$M cobalt chloride or 30 mM Tiron resulted in 6- and 8-fold increases in uPAR mRNA levels respectively. The results shown here represent 4 experiments exhibiting similar effects.

Effect of Hypoxia, Cobalt Chloride, Tiron and Carbon Monoxide on uPAR mRNA Levels To determine whether the hypoxia-mediated increases in cell surface uPAR expression reflected changes in uPAR mRNA levels, tumorigenic breast MCF-10AT3B and tumorigenic and metastatic MDA-MB-231 carcinoma cells were cultured under 1% $O_2$ for up to 24 h. Compared with culture under standard conditions, culture of MCF-10AT3B cells for as little as 2 h under hypoxic conditions resulted in a 2-fold increase in uPAR transcript levels, which increased by 4-fold in cells cultured for 16 h under hypoxia (FIG. 16). Interestingly, uPAR mRNA levels returned to control values by 24 h of hypoxic culture (FIG. 16). In contrast, uPAR transcript levels in MDA-MB-231 cells remained unchanged following 2 h of hypoxic culture but increased by 2-fold after 4 h of hypoxia, reaching a 5.5-fold increase after 24 h under hypoxia (FIG. 17). If a putative heme protein is involved in the hypoxia-mediated increase in uPAR mRNA levels, the oxy or inactive conformation of this protein can be maintained in hypoxic cells if CO is present in the hypoxic atmosphere, as this molecule binds to heme proteins and induces conformational changes in a manner similar to oxygen. In MDA-MB-231 cells, culture under hypoxic conditions for 24 h in the presence of 30% CO resulted in lower uPAR mRNA levels than in cells cultured under hypoxia alone (FIG. 17). Furthermore, culture under standard (20% $O_2$) conditions for 24 h in the presence of 100 $\mu$M cobalt chloride or 30 mM Tiron also resulted in substantial increases in uPAR mRNA levels (FIG. 18).

Secreted and Cell-associated Plasminogen Activators

Figure 19A:
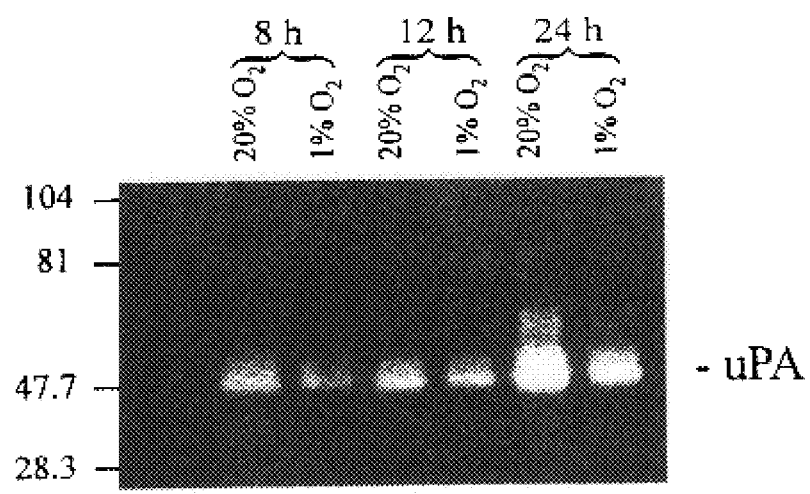
FIGS. 19A–19D show zymographic analysis of the plasminogen activator profiles in the conditioned serum-free medium of MDA-MB-231 cells. Clear areas within the gels represent caseinolytic activity resulting from activation of plasminogen. Note the presence of caseinolytic bands at 50–55 kDa which likely represent uPA (FIG. 19A and FIG. 19C), as incubation of the gels in the presence of 100 mM amiloride, an inhibitor of uPA, prevented the clearing of casein (FIG. 19B and FIG. 19D). In the absence of plasminogen, caseinolytic bands were not observed (not shown). Compared with standard cultures, plasminogen activator levels were reduced in the medium from cultures exposed to hypoxia at all time points (FIG. 19A). In contrast, cell-associated uPA levels were increased in the hypoxic cultures or in cultures treated with cobalt chloride (FIG. 19C). Furthermore, presence of CO in the hypoxic atmosphere prevented the effect of hypoxia on cell-associated uPA increases.
Figure 19B:
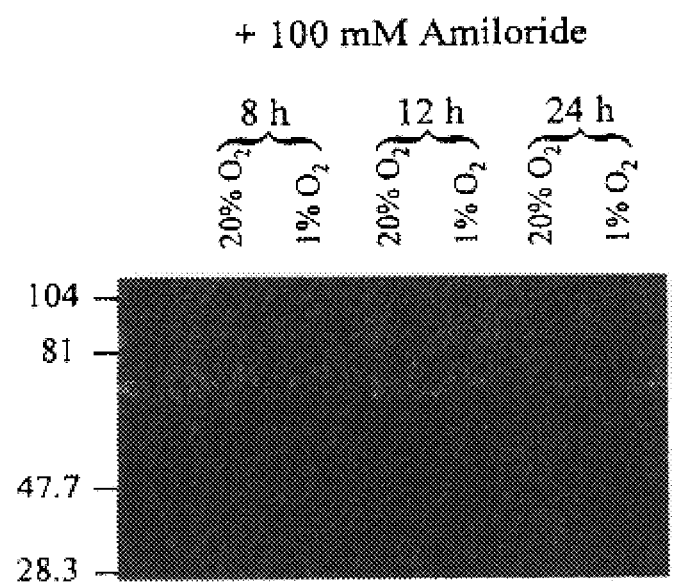
Figure 19C:
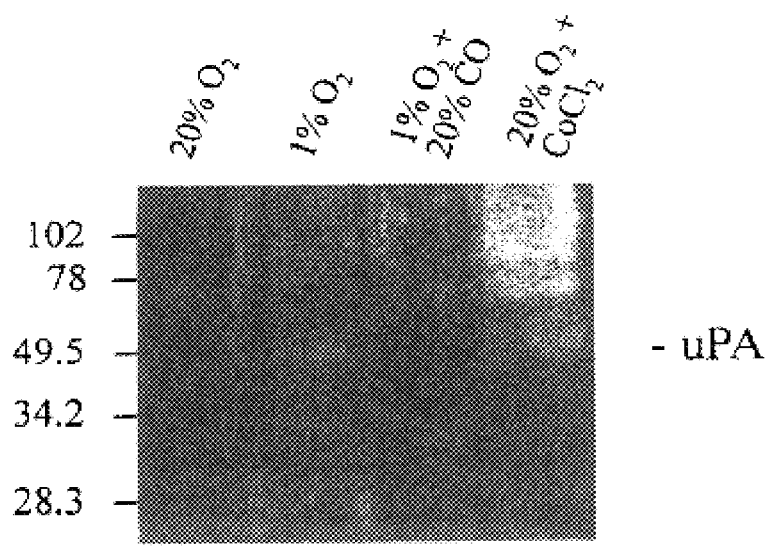
Figure 19D:
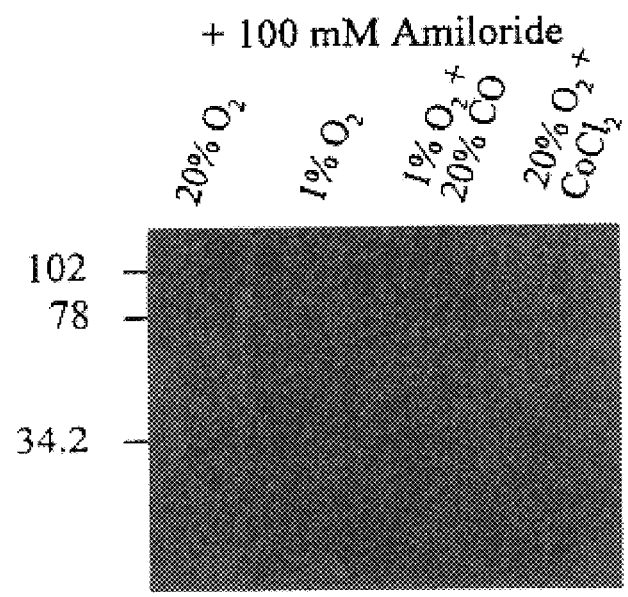

Zymographic analysis of serum-free medium conditioned by MDA-MB-231 cells for 8, 12 and 24 h under standard or hypoxic culture conditions revealed caseinolytic bands at approximately 50–55 kDa (FIG. 19A). The intensity of these bands was lower in the medium conditioned by cells cultured under hypoxia at all time points examined. By incubating the gels overnight with 100 mM amiloride, these caseinolytic bands were abolished (FIG. 19B), indicating that they represent uPA activity. If the reduction in free uPA in the culture media of cells incubated under hypoxia was due to increased binding of secreted pro-uPA to newly available uPAR, then an increased levels of cell-associated uPA would result. When extracts of cells were assessed by casein-plasminogen gel zymography, an increase in uPA levels was observed in cells cultured under 1% vs. 20% $O_2$ (FIG. 19C). Consistent with the notion that a heme protein regulates the levels of uPA-binding sites on the cell surface was the observation that culture with cobalt chloride resulted in increased cell-associated uPA. Also, incubation with 30% CO under hypoxic conditions abrogated the hypoxic increase in cell-associated uPA (FIG. 19C). In a similar manner as the conditioned media, incubation with amiloride eliminated the 50–55 kDa caseinolytic activity from cell extracts (FIG. 19D).

Effect of Hypoxia on In vitro Invasiveness

Figure 20:
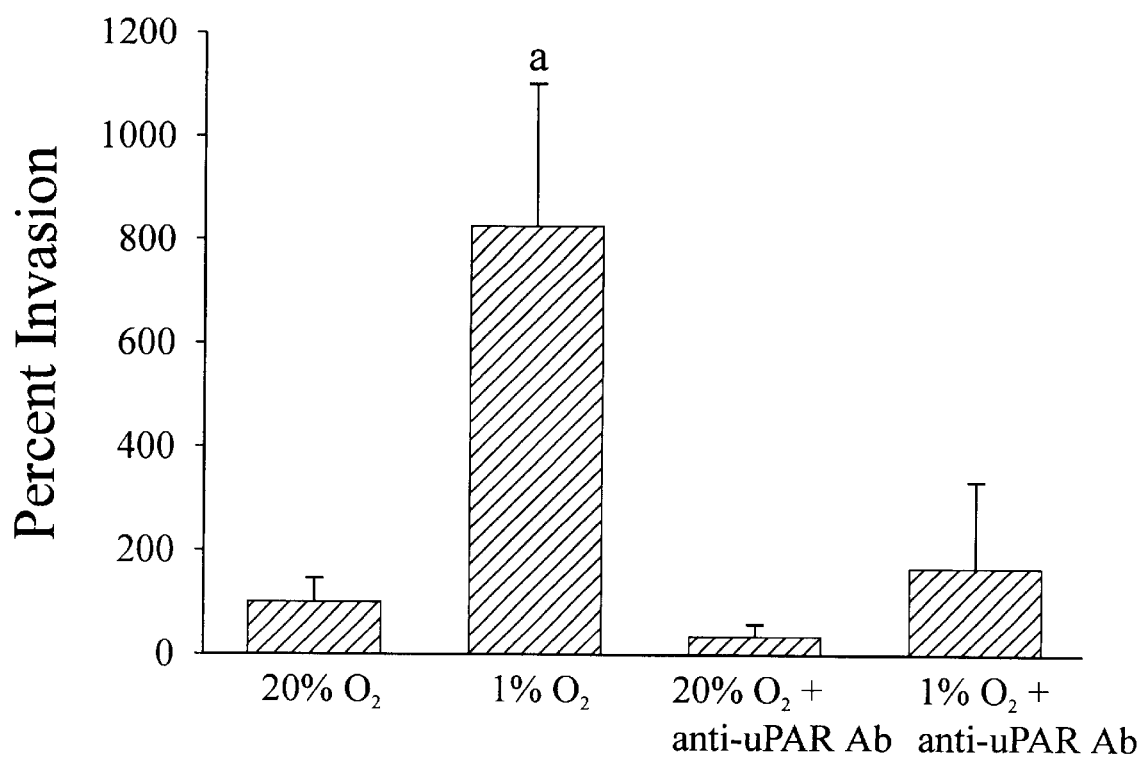
FIG. 20 is a graph illustrating in vitro invasion through Matrigel by MDA-MB-231 breast carcinoma cells. An 8-fold increase in the number of cells reaching the underside of the polycarbonate membrane was observed when the assay was performed under 1% $O_2$ as compared to 20% $O_2$. Presence of 10 $\mu$g/ml anti-uPAR mAb 3936 under hypoxic conditions abrogated the effect of low oxygen on invasion. Bars represent the mean number of cells that invaded in 6 independent assays±standard error

To determine a functional correlate of increased uPAR levels in hypoxic cultures, the effect of exposure to low levels of oxygen on the ability of tumor cells to invade Matrigel in vitro was assessed. In one series of tests, MDA-MB-231 cells exhibited an invasion index 40% higher under 1% $O_2$ than under standard conditions (p<0.01, Student=s t-test; N=15). This hypoxia-mediated increase in invasiveness was completely abrogated by inclusion of 30% CO in the hypoxic atmosphere (not shown), suggesting also the involvement of a heme protein on the effect of hypoxia on invasion. Another set of tests were performed to determine whether the increased invasiveness observed under hypoxia is directly linked to uPAR upregulation. The inclusion of a blocking anti-uPAR antibody (3936) with the cells at the initiation of the invasion assay abolished the effect of hypoxia on invasion (FIG. 20). The presence of this antibody also resulted in a 65% reduction in the invasiveness of cells incubated under standard conditions, suggesting that finctional uPAR is required for basal levels of invasion.

Discussion

The results of this study demonstrate the up-regulated expression of genes (uPAR, PAI-1 and RTP/Drg1) in various cell types cultured under low levels of oxygen. The expression of RTP/Drg1 has also been shown to be increased in endothelial cells treated with homocysteine (Kokame, K., et al. *J Biol Chem* 271:29659–29665 (1996)) as well as during differentiation of colon epithelial cells (van Belzen, N., et al. *Lab Invest* 77:85–92 (1997)) and in human lung A549 cells exposed to nickel (Zhou, D., et al., *Cancer Res* 58:2182–2189 (1998)).

RTP/Drg1, uPAR and PAI-1 can be added to the growing list of oxygen-regulated genes of mammalian cells which include those encoding key enzymes of the glycolytic pathway (Semenza, G. L., et al., *J.Biol.Chem* 269:23757–23763 (1994)), erythropoietin (Goldberg, M. A., et al, *Science* 242:1412–1415 (1988)), vascular endothelial growth factor (VEGF) (Forsythe, J. A., et al., *Mol. Cell.Biol* 16:4604–4613 (1996)) and heme oxygenase-1 (Lee, P. J., et al, *J Biol Chem* 272:5375–5381 (1997)) among several. The mechanism by which hypoxia stimulates expression of some of the above genes appears to involve transcriptional activation by nuclear factors such as hypoxia inducible factor-1 (HIF-1) (Forsythe, J. A., et al, *Mol.Cell.Biol.* 16:4604–4613 (1996)), AP-1 and NF-κB (Rupec, R. A. and Baeuerle, P. A. *Eur.J-.Biochem.* 234:632–640 (1995)). HIF-1 is a heterodimeric protein, composed of a HIF-1α and a HIF-1β subunit, first identified as a DNA-binding activity that recognized a DNA sequence in the hypoxia-inducible enhancer of the erythropoietin gene (Semenza, G. L. and Wang, G. L. *Mol. Cell-.Biol.* 12:5447–5454 (1992)). More recent studies have revealed that HIF-1 plays an important role in the hypoxia-mediated inhibition of cellular proliferation and induction of apoptosis (Carmeliet, P., et al., *Nature* 394:485–490 (1998)). Elucidation of the sequences flanking the gene, can determine whether HIF-1 and/or other transcription factors are involved in the hypoxic up-regulation of RTP/Drg1 expression.

The results of this study suggest that the hypoxic up-regulation of uPAR, PAI-1 and RTP/Drg1 is mediated through an oxygen-sensing heme protein. This conclusion is based on the results of experiments in which the ability of such a protein to regulate uPAR, PAI-1 or RTP/Drg1 expression was evaluated through the use of molecules like cobalt chloride, Tiron and DFO, which mimic hypoxia by preventing the binding of oxygen to the heme moiety of the putative oxygen-sensing protein (cobalt), or by blocking heme biosynthesis (Tiron and DFO). The fact that incubation with these three compounds led to similar observations suggests that the results were due to inhibition of a heme-containing protein and not due to non-specific effects. Furthermore, we also showed that the up-regulation of uPAR, PAI-1 and RTP/Drg1 expression in response to hypoxia was blocked by carbon monoxide. Since carbon monoxide was unable to inhibit the up-regulation of RTP/Drg1 expression induced by cobalt chloride, Tiron and DFO, it indicates that its effect was not due to non-specific toxicity. Interestingly, when the RTP/Drg1 gene was cloned independently by Zhou et al (Zhou, D., et al., *Cancer Res* 58:2182–2189 (1998)) (named Cap43 by these investigators), it was found to be induced by nickel, a molecule that also replaces ferrous iron from heme proteins and which does not bind oxygen. It is possible that, in their study, the up-regulation of RTP/Drg1 in lung epithelial cells in response to nickel exposure was due to the heme protein-blocking properties of nickel and not due to its carcinogenic effects.

The described study also revealed that the 43-kDa protein encoded by the RTP/Drg1 gene localizes to the hypoxic, deeper regions of multicellular spheroids cultured under 20% oxygen. However, culture of cell aggregates under 1% oxygen resulted in widespread immunolocalization of the protein, even in the superficial layers of the spheroids. Three-dimensional cell cultures have been used extensively to study the role of oxygen levels in various aspects of tumour biology including sensitivity to chermotherapy and radiation, metabolism, invasion and metastasis, and angiogenesis (Mueller-Klieser, W. *Am J Physiol* 273:C1109–C1123 (1997)). Since low intratumoral oxygen levels are associated with a poor clinical prognosis (Brizel, D. M., et al., *Int.J.Radiation Oncology Biol.Phys.* 38:285–289 (1997); Höckel, M., et al., *Cancer Res.* 56:4509–4515 (1996); Brizel, D. M., et al., *Cancer Res.* 56:941–943 (1996)), the 43-kDa protein described in our study may be a good marker of hypoxic regions within the tumor mass and therefore of prognostic significance.

The present findings demonstrated substantially increased RTP/Drg1 expression in cells incubated under 1% and 2% oxygen compared to cells cultured at or above 4% oxygen. These results may be of physiologic and clinical relevance, as most tissues in the body are exposed to oxygen concentrations equivalent to 5% or lower. This study also showed that the high levels of expression of RTP/Drg1 protein persisted for at least 72 h following a hypoxic stimulus, indicating a relatively slow turnover of this protein. In contrast, the increased expression of cell surface urokinase receptors in response to hypoxia returns to background levels about 45 minutes following reoxygenation. The fact that cellular RTP/Drg1 expression remains high for an extended period following transient exposure to low levels of oxygen may also be relevant to conditions in which relatively short periods of exposure to hypoxia occur, such as during temporary vasoconstriction, sleep apnea, or fetal hypoxia. The described findings suggest that such episodes of hypoxia may lead to long-lasting phenotypic changes. Since our results show an inverse correlation between oxygen concentration and RTP/Drg1 expression, assessment of the levels of this protein may be useful in determining the extent of oxygen deprivation in the above settings. Our data reveal increased RTP/Drg1 mRNA levels in hypoxic, peri-infarct regions of placentae of preeclamptic women compared to non-infarct areas or normal placentae.

EXAMPLE 6

Materials and Methods

Animals 16 adult male Wistar rats from Charles River Laboratories (Montreal, Quebec) weighing 300–350 g were used in the investigation. The animals were divided into two study groups. The animals were individually housed in a climate-controlled room under a 12-hour light/dark cycle and allowed access to food (Purina Lab Chow) and water ad libitum. All procedures were in accordance with the guidelines set out by the Canadian Council on Animal Care. The animals were allowed to acclimate 5 days prior to testing and were handled by the researcher during this time.

Experimental Procedure

The apomorphine (APO) bioassay of erectile function was performed in an isolated area. The rat model of APO-induced erections used to assess the effects of p,p-DDE and flutamide on erectile function was based on the model developed by Heaton et al *J Urol.* 145:1099 (1991). The animals were each placed in a separate hanging wire test cage in an isolated, dark and sound proof room and allowed to acclimatize to the surroundings for 10 minutes. Each rat received 80 ug/kg APO (Sigma Chemical Co., St. Louis, Mo.) prepared in physiological saline containing 100 ug/kg ascorbic acid via subcutaneous (s.c.) injection (lml/kg at the nape of the neck). Erectile and yawning responses to APO were monitored and recorded (30 minutes) in an adjacent room via a video monitoring system.

An erection was counted when an engorged glans penis and distal shaft were exposed. A wide opening of the mouth associated with appropriate respiratory movement identified a yawn. Prior to the commencement of each study, each group of eight rats were pre-tested with APO to ensure that each rat had a normal 'control' erectile response. Rats with unsatisfactory control erectile response were removed from further study.

Figure 21:
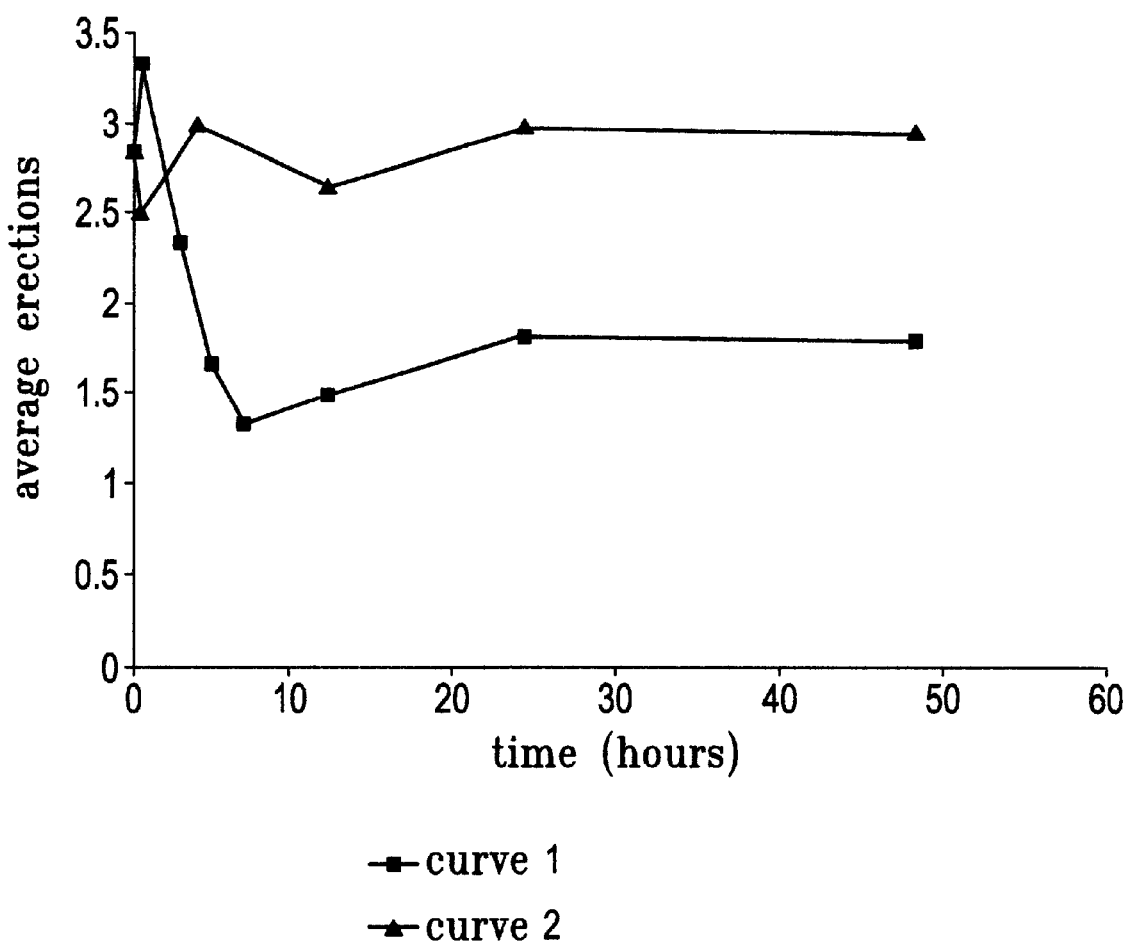
FIG. 21 is a graph showing APO-induced erections at different frequencies of APO administration. Curve 1 shows erectile response at administration frequencies of 0.5, 3, 5, 7, 12, 24, 48 hours after initial time point. Curve 2 shows erectile response at administration intervals of 0.5, 4, 12, 24, 48 hours after initial time point (n=6).

In order to develop a suitable APO-testing protocol during the p,p-DDE treatments, two different time series of administrations were used in preliminary experiments (n=6 rats). Series 1 involved APO-treatments at 7 time points (0.5, 3, 5, 7, 12, 24, 48 hours) over 2 days. In Series 2, performed 3–4 weeks later, we used only 5 time points (0.5, 4, 12, 24, 48 hours) over 2 days. The results of this methodological study (FIG. 21) clearly revealed that the Series 2 protocol of APO administrations provided a more reproducible means of testing erectile responses. The more frequent Series 1 protocol showed a persistent decrease in erectile responses over the time course. Yawns were not altered in either protocol (data not shown). Based on the results of this study all subsequent time course testing used the Series 2 time course (0.5, 4, 12, 24, 48 hours). Study 1: Preliminary assessment of p,p-DDE effects The doses of p,p-DDE were derived from the literature. According to Gray et al *Physiol. & Behav.* 24:463 (1980), daily subcutaneous administration of flutamide (25 mg/kg) caused a significant decrease in erections. As shown by Kelce et al, p,p-DDE has approximately one tenth the affinity for androgen receptors compared to flutamide Kelce et al *Nature.* 375:581 (1995). Accordingly, based on the studies by Gray et al and Kelce et al the initial dose of p,p-DDE (270 mg/kg) was calculated to provide a equi-effective dose compared to flutamide (25 m/kg).

Six rats were each administered on separate occasions a single dose of 270 mg/kg or 500 mg/kg p,p-DDE (Aldrich Chemical Co., Milwaukee, Wis.) dissolved in peanut oil. The 270 mg/kg dose was prepared, requiring initial heating and stirring. This dose was administered in a single injection (1 ml/kg, i.p. of a 270 mg/ml concentration) half an hour prior to the commencement of APO-induced erectile monitoring. The second dose of p,p-DDE (500 mg/kg) was administered one week after the initial dose of 270 mg/kg. The 500 mg/kg dose of p,p-DDE was prepared in a 250 mg/ml concentration and administered in a single injection (2 ml/kg i.p.) half an hour prior to the commencement of APO-induced erectile monitoring.

Study 2a: Flutamide Administration

Eight rats were treated with APO to determine baseline erectile and yawning response. The following day, rats were subject to a control series of APO tests at intervals of 0.5, 4, 12, 24, 48 hours after a starting time.

At one week intervals, rats were given single, increasing doses of flutamide (25, 35, or 50 mg/kg) (Sigma Chemical Co., St. Louis, Mo.). For each dose, flutamide was dissolved in peanut oil and administered via i.p injection in a volume of 1 ml/kg. Rats were tested with APO up to 48 hours at the intervals used for the control series (determined in Study 1). Each dose of flutamide was given 1 week after the previous dose, to allow APO-induced erections to return to control levels.

Study 2b: Time Course of p,p-DDE Depression of APO Induced Erections

One week after completion of the flutamide investigation, rats were subjected to a control series of APO tests to determine that erectile response had returned to baseline. From the group of 8 rats, 4 rats were randomly selected. These rats were subsequently given 500 mg/kg p,p-DDE (prepared and administered as described in Study 1). APO-induced erections and yawns were monitored for 2 weeks at APO-testing intervals of 0.5, 4, 12, 24, 48, 72 hours, 1 week, 2 weeks to determine the time course of p,p-DDE depression of APO-induced erectile response.

Study 2c: Testosterone Supplementation

Two weeks after p,p-DDE administration, rats were given testosterone supplementation in single doses (480 ug/kg, 1.2 or 2.4 mg/kg, i.p.) with each dose administered on a separate occasion. The initial dose of 480 ug/kg was derived from the Heaton and Varnin of testosterone supplementation of castrated rats (Heaton, J. P. W. and Varrin, S. J. *J. Urol.* 151:797(1994)). Testosterone was administered in an attempt to recover APO-induced erections to control levels.

For each dose of testosterone, APO-induced erections were monitored over 12 hours at APO-testing intervals of 0.5, 4, 12 hours after testosterone administration. Each dose of testosterone was given 48 hours after the previous dose. The required testosterone concentrations were prepared using 100 mg/ml testosterone propionate (Taro Pharmaceuticals, Brarnalea, ON.) diluted in peanut oil. Each dose was administered in a 1 ml/kg volume. The remaining 4 rats from the initial group of 8 (not treated with p,p-DDE) were used as controls for the p,p-DDE treated rats. APO responses of the testosterone supplemented p,p-DDE treated rats were compared to the APO responses of the 4 control rats using a Student's unpaired t-test.

Statistical Analysis

For each APO testing protocol, the average number of erections and standard deviation was determined. Prior to any treatment, each rat underwent similar APO-testing intervals to determine control APO-induced erections. Therefore, each rat served as its own control. Treated values were compared to control values using Student's paired t-test, except where noted in Study 2b.

Results

Study 1: p,p-DDE Administration

The 500 mg/kg dose showed a significant decrease in apomorphine (APO)-induced erectile response 3 hours after p,p-DDE administration. The 270 mg/kg dose of p,p-DDE had no significant effect on APO-induced erections over the 5 hour testing period. APO-induced yawning responses were not altered by the p,p-DDE treatment (data not shown).

Study 2a: Flutamide Administration

Figure 22:
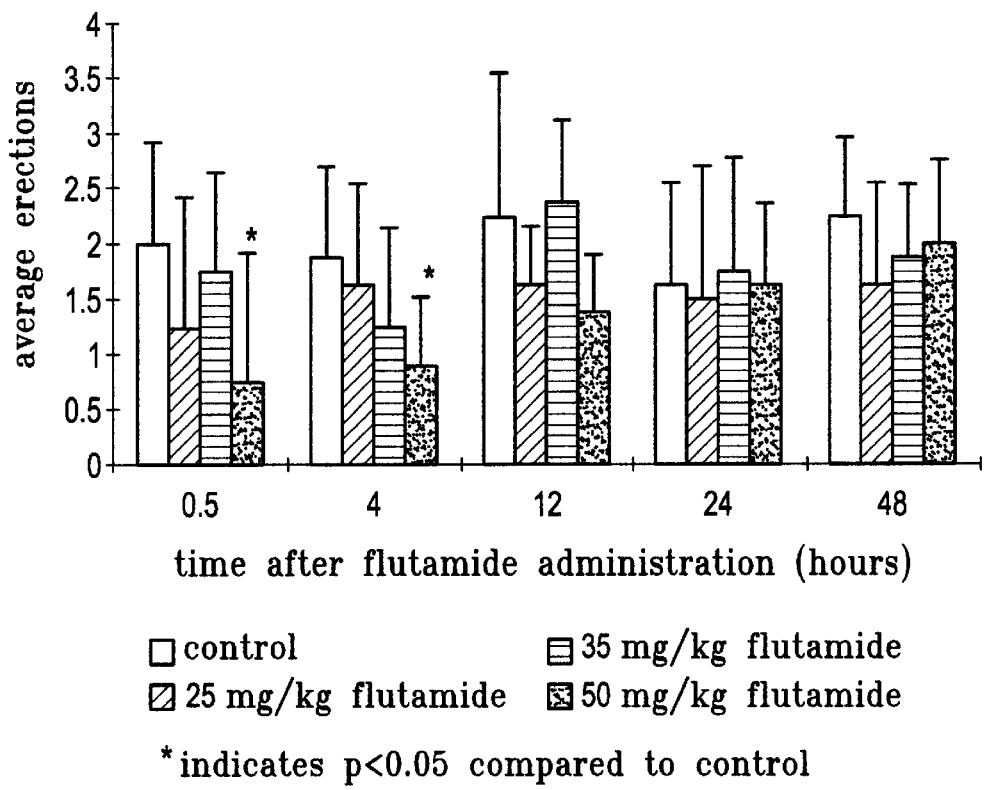
FIG. 22 is a graph showing APO-induced erectile response after a single administration of 25, 35 and 50 mg/kg flutamide at intervals of 0.5, 4, 12, 24, 48 hours after flutamide administration (n=8).

The results from the dose-ranging study of flutamide on APO-induced erections are presented in FIG. 22. A decrease in APO-induced erections was found only at the highest dose of flutamide at 0.5 and 4 hours after drug administration although there appeared to be a trend at lower doses. Normal APO-induced erectile responses were obtained at all doses 24 hours following flutamide administration.

The 50 mg/kg dose of flutamide also caused a significant decrease in the yawning response to APO at 4, 12 and 24 hours after flutamide administration. In contrast, the 25 and 35 mg/kg doses of flutamide did not effect APO-induced yawns.

Study 2b: Time Course of p,p-DDE Depression of APO Induced Erections

Figure 23:
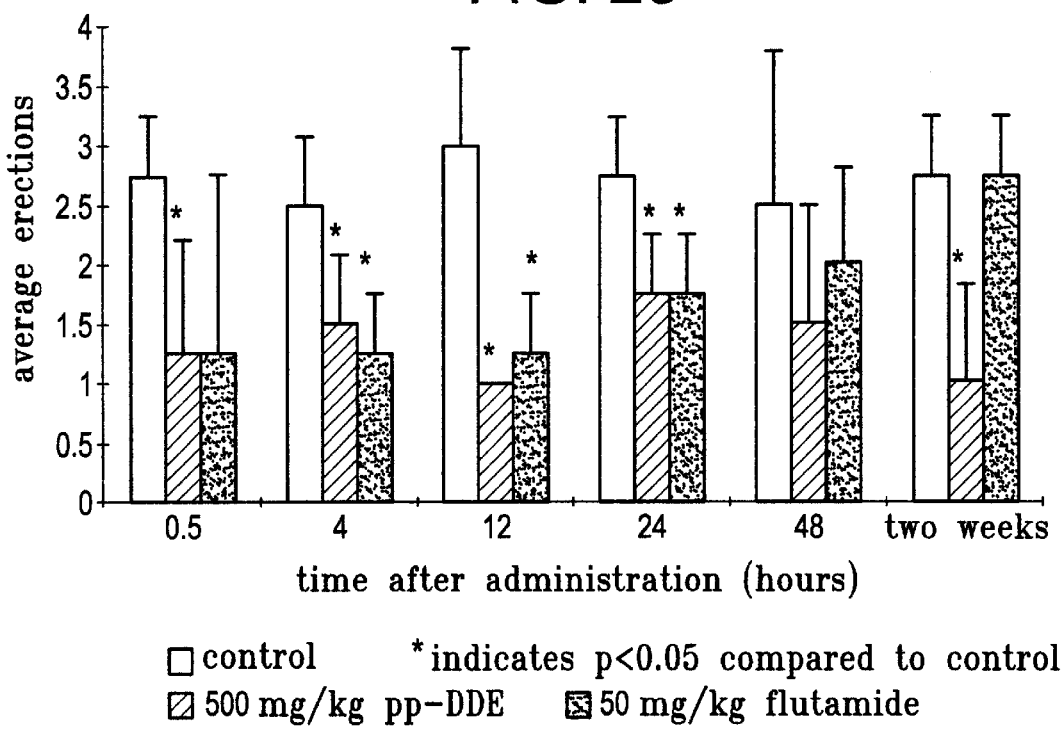
FIG. 23 is a graph showing APO-induced erections after administration of 50 mg/kg flutamide (n=4) and 500 mg/kg p,p-DDE (n=4) at intervals of 0.5, 4, 12, 24, 48 hours and 2 weeks after compound administration. At two weeks, p,p-DDE erectile response was significantly different from both control and 50 mg/kg flutamide responses.
Figure 25A:
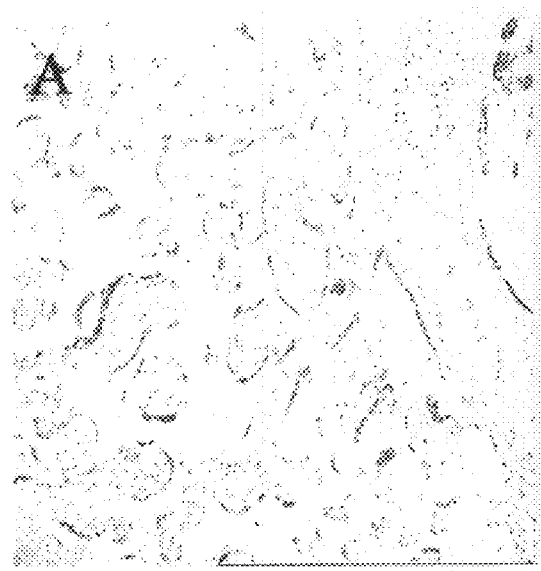
FIG. 25A is a bright field photomicrograph of normal chorionic villi obtained at full gestation.
Figure 25B:
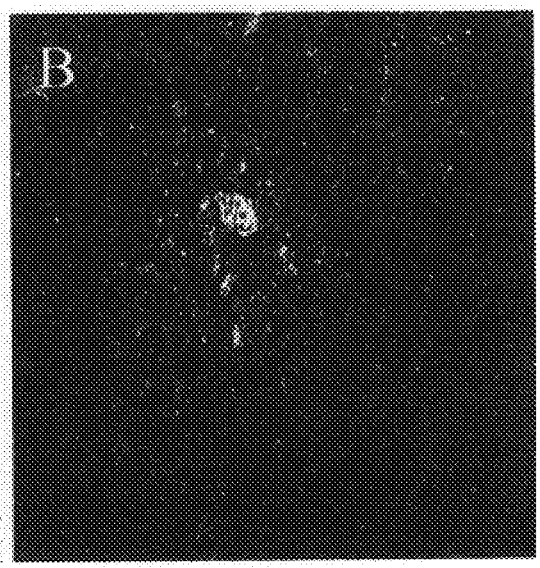
FIG. 25B is a dark field photomicrograph of the normal chorionic villi shown in FIG. 25A. The tissue section was incubated with antisence radiolabeled RTP/Drg1 cRNA probe. The white dots are hybridization grains which are indicative of RTP/Drg1 (PROXY-1) mRNA expression.
Figure 25C:
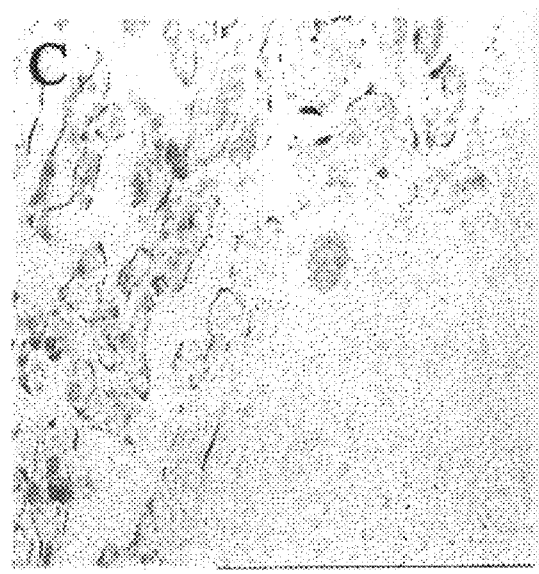
FIG. 25C is a bright field photomicrograph of preeclamptic chorionic villi obtained at full gestation.
Figure 25D:
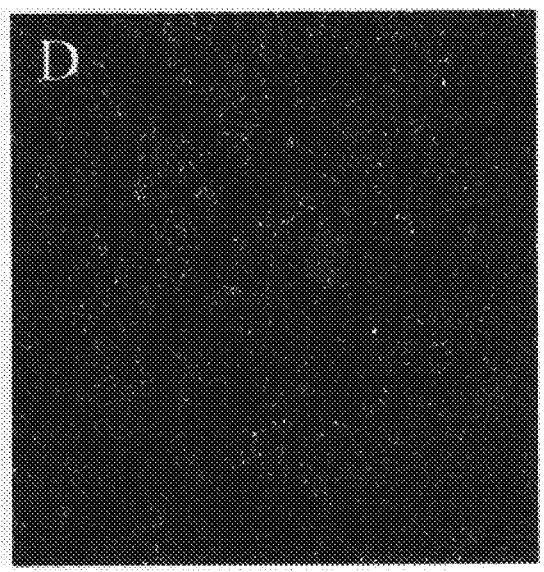
FIG. 25D is a dark field photomicrograph of the preeclamptic chorionic villi shown in FIG. 25C. The tissue section was incubated with antisence radiolabeled RTP/Drg1 cRNA probe. The white dots are hybridization grains which are indicative of RTP/Drg1 (PROXY-1) mRNA expression. Note the higher number of hybridization grains in tissue isolated from preeclamptic pregnancies compared with normal tissue (compare FIGS. 25D and 25B).

Results from the time course assessment of p,p-DDE suppression of APO-induced erections are shown in FIG. 23. APO-induced erections were significantly decreased at 0.5, 4, 12, 24 hours and 2 weeks after administration of a single dose of 500 mg/kg p,p-DDE. FIG. 23 also compares the suppression of APO-induced erections after 500 mg/kg p,p-DDE and 50 mg/kg flutamide. APO-induced erections with flutamide administration returned to control levels 48 hours after flutamide administration (n=4). p,p-DDE persistently suppressed APO-induced erections over the two week testing period. Two weeks after p,p-DDE administration, APO-induced erections were significantly different from controls and from the flutamide two week response.

APO-induced yawns over the two week assessment of p,p-DDE were not significantly different from control levels.

Study 2c: Testosterone Supplementation

Two weeks after administration of 500 mg/kg p,p-DDE, APO-erections remained significantly lower than controls. Testosterone was administered to return APO-induced erections to control levels. Results from testosterone supplementation on APO-induced erections are shown in FIG. 24. For each dose of testosterone, there were no significant increases in erections compared to the levels of erections in p,p-DDE treated rats. Similarly, compared to control levels, APO-induced erections with all doses of testosterone remained significantly decreased at most of the time points of APO testing.

Administration of p,p-DDE had little effect on APO-induced yawns; subsequent administration of testosterone did not change the status of yawning responses over the 12 hour test periods.

Discussion

The present study demonstrates that an environmental chemical, such as p,p-DDE, can negatively impact vascular condition, specifically, erectile function. Using the apomorphine (APO) bioassay of erectile responses two specific findings were that: (i) although both p,p-DDE and flutamide could decrease erections acutely, p,p-DDE caused a persistent decrease in APO-induced erectile function for longer than 2 weeks; and (ii) administration of even high doses of testosterone beginning at 2 weeks after p,p-DDE administration failed to return APO-induced erections to control levels.

The transient suppression of APO-induced erections by the non-steroidal androgen receptor antagonist flutamide (i.e. the return to control levels within 24 hours) is consistent with the known pharmacokinetic and pharmacodynamic profile of this drug (Berson, A., et al., *J. Pharm. Exp. Ther.* 265(l):366 (1993)). In contrast, the persistent suppression of APO-induced erectile response for more than two weeks following a single administration of p,p-DDE, albeit a high dose, is in agreement with the known persistence and bioaccumulating capacity of this environmental contaminant. The dose of p,p-DDE which produced the erectolytic effect was 10 fold greater than for flutamide. This is compatible with the results in vitro involving androgen receptor binding studies demonstrating that the affinity of p,p-DDE is 10 fold less than flutamide (Kelce, W. R., et al., *Nature.* 375:581 (1995)). Thus, the similar acute decrease in APO-induced erections with both p,p-DDE and flutamide and the persistent of only the p,p-DDE effect can be explained by the marked differences in clearance of the two xenobiotics. Flutamide is rapidly metabolised by hepatic cytochromes P450 in both rats and humans upon administration (Berson, A., et al., *J. Pharm. Exp. Ther.* 265(1):366 (1993)). In contrast, upon absorption p,p-DDE is not metabolised (Feldman, H. A., et al., *J. Urol.* 151:54 (1994)) but rather incorporates into adipose tissue and other lipid-containing tissues due to its lipophilicity. Therefore, a single dose of p,p-DDE is retained in body tissues over a long period of time (perhaps indefinitely) whereas a single dose of flutamide is metabolised immediately after administration and does not persist in the body.

The effects of p,p-DDE on plasma testosterone levels found in the literature are somewhat inconclusive. The present results involving the lack of effect of high dose testosterone supplementation in rats previously treated with p,p-DDE do not suggest an obvious mechanism. Interestingly, studies by Kelce et al found that administration of p,p-DDE did not alter plasma testosterone levels in pubertal or adults rats (Kelce, W. R., et al., *Nature.* 375:581 (1995)), although the level of androgen receptor antagonism was not determined. Our findings that even high dose testosterone supplementation failed to return APO-induced erections to previously treated p,p-DDE-rats potentially suggests very prolonged receptor blockade but without involving 'typical' compensatory feedback upregulation of testosterone production.

The evidence suggesting that environmental contaminants can contribute to erectile dysfunction represents a novel line of epidemiological thinking. Current epidemiology surrounding endocrine disrupters and reproduction in human beings has primarily focussed on the potential effects of these contaminants on sperm production and abnormalities in male and female reproductive system development as well as increased incidences of hormone-dependent cancers (Carlsen, E., et al., *B.M.J.* 305(6854):609 (1992)). Although these previous studies provide relevant background information, they have, for the most part, overlooked the importance of vascular condition (e.g., erectile function) as a critical component of reproductive function.

In conclusion, the findings described herein support the concept of the role of oxygen as an important regulator of gene expression and cell phenotype, and thus, provide a scientific basis for diagnosing vascular conditions associated with a reduction in blood flow, hypoxic conditions and endothelial dysfunction.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for diagnosing hypoxia in an individual comprising:
    (a) measuring an RTP/Drg1 gene product level in a biological sample obtained from an individual; and
    (b) comparing the measured RTP/Drg1 gene product level in the biological sample to RTP/Drg1 gene product level in a reference sample, wherein an increase in the RTP/Drg1 gene product level in the biological sample as compared to the level in the reference sample is indicative of hypoxia.

2. The method of claim 1 wherein said biological sample and said reference sample are obtained from the same individual.

3. The method of claim 2 wherein said reference sample is obtained prior to the onset of said hypoxia.

4. The method of claim 1 wherein said gene product is RNA.

5. The method of claim 1 wherein said gene product is a polypeptide or an antibody binding fragment thereof.

6. The method of claim 1 wherein said biological sample is selected from the group consisting of leukocytes, blood, serum, plasma, saliva, urine and tissue.

7. The method of claim 1 wherein the hypoxia is chronic.

8. The method of claim 1 wherein the hypoxia is transient.

9. The method of claim 1 wherein the hypoxia is diagnosed post-mortem and used to determine time and/or cause of death.

10. The method of claim 1 wherein the individual is suffering from a tumor and the diagnosis of hypoxia indicates poor prognosis.

11. A method for diagnosing preeclampsia in a pregnant woman comprising:
    (a) measuring an RTP/Drg1 gene product level in a biological sample obtained from a pregnant woman; and
    (b) comparing the measured RTP/Drg1 gene product level in the biological sample to RTP/Drg1 gene product level in a reference sample, wherein an increase in the RTP/Drg1 gene product level in the biological sample as compared to the level in the reference sample is indicative of preeclampsia.

12. The method of claim 11 wherein said biological sample and said reference sample are obtained from the same individual.

13. The method of claim 11 wherein said reference sample is obtained prior to the onset of said preeclampsia.

14. The method of claim 11 wherein said gene product is RNA.

15. The method of claim 11 wherein said gene product is a polypeptide or an antibody binding fragment thereof.

* * * * *

UNITED STATES PATENT AND TRADEMARK OFFICE
CERTIFICATE OF CORRECTION

PATENT NO. : 6,376,169 B1
DATED : April 23, 2002
INVENTOR(S) : Adams et al.

It is certified that error appears in the above-identified patent and that said Letters Patent is hereby corrected as shown below:

<u>Title page,</u>
Item [75], please delete ";Susan E. Brien, both of"

Signed and Sealed this

Nineteenth Day of November, 2002

*Attest:*

*Attesting Officer*

JAMES E. ROGAN
*Director of the United States Patent and Trademark Office*